United States Patent
Hamilton et al.

(10) Patent No.: US 6,194,062 B1
(45) Date of Patent: *Feb. 27, 2001

(54) STORAGE WRAP MATERIAL

(75) Inventors: Peter Worthington Hamilton, Cincinnati; Kenneth Stephen McGuire, Wyoming, both of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/745,340

(22) Filed: Nov. 8, 1996

Related U.S. Application Data

(63) Continuation-in-part of application No. 08/584,638, filed on Jan. 10, 1996, now Pat. No. 5,662,758.

(51) Int. Cl.[7] .................................................. B32B 31/00

(52) U.S. Cl. .......................................... 428/343; 428/354

(58) Field of Search ...................................... 428/343, 354

(56) References Cited

U.S. PATENT DOCUMENTS

| | | | |
|---|---|---|---|
| D. 373,026 | 8/1996 | Delebreau et al. | D5/20 |
| 2,861,006 | 11/1958 | Salditt | 117/7 |

(List continued on next page.)

FOREIGN PATENT DOCUMENTS

| | | | |
|---|---|---|---|
| 570960 | 12/1961 | (BE) . | |
| 0 037 101 A1 | 10/1981 | (EP) | B65D/77/20 |

(List continued on next page.)

OTHER PUBLICATIONS

Broughton, J., et al., "Porous Cellular Ceramic Membranes: A Stochastic Model To Describe the Structure of an Anodic Oxide Membrane", Journal of Membrane Science 106, pp. 89–101 (1995).

(List continued on next page.)

*Primary Examiner*—Terrel Morris
*Assistant Examiner*—Cheryl Juska
(74) *Attorney, Agent, or Firm*—Thomas J. Osborne, Jr.; Leonard W. Lewis; Stephen W. Miller

(57) ABSTRACT

The present invention relates to sheet-like materials suitable for use in the containment and protection of various items, as well as the preservation of perishable materials such as food items. More particularly, the present invention provides an improved storage wrap material comprising a sheet of material having a first side and a second side. The first side comprises an active side exhibiting an adhesion peel force after activation by a user which is greater than an adhesion peel force exhibited prior to activation by a user. The storage wrap material may be activated by different approaches, but in a preferred embodiment the active side is activatible by an externally applied force exerted upon the sheet of material. The force may be an externally applied compressive force exerted in a direction substantially normal to the sheet of material. In accordance with the present invention, the storage wrap material is selectively activatible by a user in discrete regions to provide adhesive properties where and when desired. The use of an adhesive or adhesive-like substance on the surface of the material provides an adhesion peel force after activation which is sufficient to form a barrier seal against a target surface at least as great as those of the material and the target surface such that perishable items, such as food items, may be effectively preserved. The storage wrap materials of the present invention may be utilized to enclose and protect a wide variety of items by various methods of application, including direct application to the desired item, enclosure of the desired item and securement to itself, and/or in combination with a semi-enclosed container.

24 Claims, 6 Drawing Sheets

U.S. PATENT DOCUMENTS

| | | | |
|---|---|---|---|
| 3,312,005 | 4/1967 | McElroy | 40/2 |
| 3,386,846 | 6/1968 | Lones | 117/11 |
| 3,554,835 | 1/1971 | Morgan | 156/234 |
| 3,592,722 | 7/1971 | Morgan | 161/148 |
| 3,853,129 | 12/1974 | Kozak | 128/287 |
| 3,879,330 | 4/1975 | Lustig | 260/31.8 M |
| 3,901,237 | 8/1975 | Cepuritis et al. | 128/284 |
| 3,937,221 | 2/1976 | Tritsch | 128/287 |
| 3,943,609 | 3/1976 | Egan, Jr. | 24/73 |
| 3,967,624 | 7/1976 | Milnamow | 128/287 |
| 4,023,570 | 5/1977 | Chinai et al. | 128/290 R |
| 4,054,697 | 10/1977 | Reed et al. | 428/40 |
| 4,061,820 | 12/1977 | Magid et al. | 428/311 |
| 4,067,337 | 1/1978 | Ness | 128/287 |
| 4,181,752 | 1/1980 | Martens et al. | 427/54.1 |
| 4,273,889 | 6/1981 | Yamazaki et al. | 525/109 |
| 4,303,485 | 12/1981 | Levens | 204/159.24 |
| 4,336,804 | 6/1982 | Roeder | 128/290 R |
| 4,337,772 | 7/1982 | Roeder | 128/290 R |
| 4,339,088 | 7/1982 | Niedermeyer | 242/1 |
| 4,342,314 | 8/1982 | Radel et al. | 128/287 |
| 4,376,440 | 3/1983 | Whitehead et al. | 604/387 |
| 4,392,897 | 7/1983 | Herrington | 156/66 |
| 4,397,905 | 8/1983 | Dettmer et al. | 428/180 |
| 4,404,242 | 9/1983 | Suier | 428/35 |
| 4,405,666 | 9/1983 | Squier | 428/35 |
| 4,410,130 | 10/1983 | Herrington | 383/62 |
| 4,460,634 | 7/1984 | Hasegawa | 428/124 |
| 4,508,256 | 4/1985 | Radel et al. | 228/152 |
| 4,509,908 | 4/1985 | Mullane, Jr. | 425/290 |
| 4,514,345 | 4/1985 | Johnson et al. | 264/22 |
| 4,519,095 | 5/1985 | Clayton | 383/86 |
| 4,528,239 | 7/1985 | Trokhan | 428/247 |
| 4,556,595 | 12/1985 | Ochi | 428/143 |
| 4,576,850 | 3/1986 | Martens | 428/156 |
| 4,578,069 | 3/1986 | Whitehead et al. | 604/370 |
| 4,587,152 | 5/1986 | Gleichenhagen et al. | 428/195 |
| 4,612,221 | 9/1986 | Biel et al. | 428/35 |
| 4,655,761 | 4/1987 | Grube et al. | 604/389 |
| 4,659,608 | 4/1987 | Schulz | 428/171 |
| 4,695,422 | 9/1987 | Curro et al. | 264/504 |
| 4,699,622 | 10/1987 | Toussant et al. | 604/389 |
| 4,743,242 | 5/1988 | Grube et al. | 604/389 |
| 4,778,644 | 10/1988 | Curro et al. | 264/557 |
| 4,803,032 | 2/1989 | Schulz | 264/284 |
| 4,820,589 | 4/1989 | Dobreski et al. | 428/422 |
| 4,839,216 | 6/1989 | Curro et al. | 428/134 |
| 4,894,275 | 1/1990 | Pelzer | 428/166 |
| 4,946,527 | 8/1990 | Battrell | 156/60 |
| 4,959,265 | 9/1990 | Wood et al. | 428/343 |
| 5,008,139 | 4/1991 | Ochi et al. | 428/40 |
| 5,080,957 | 1/1992 | Leseman et al. | 428/167 |
| 5,098,522 | 3/1992 | Smurkoski et al. | 162/358 |
| 5,112,674 | 5/1992 | German et al. | 428/216 |
| 5,116,677 | 5/1992 | Jones | 428/349 |
| 5,141,790 | 8/1992 | Calhoun et al. | 428/40 |
| 5,175,049 | 12/1992 | Huff et al. | 428/218 |
| 5,176,939 | 1/1993 | Shepherd | 427/146 |
| 5,208,096 | 5/1993 | Dohrer | 428/218 |
| 5,221,276 | 6/1993 | Battrell | 604/389 |
| 5,245,025 | 9/1993 | Trokhan et al. | 536/56 |
| 5,246,762 | 9/1993 | Nakamura | 428/172 |
| 5,269,776 | 12/1993 | Lancaster et al. | 604/387 |
| 5,273,809 | 12/1993 | Simmons | 428/212 |
| 5,275,588 | 1/1994 | Matsumoto et al. | 604/372 |
| 5,296,277 | 3/1994 | Wilson et al. | 428/40 |
| 5,310,587 | 5/1994 | Akohori et la. | 428/35.2 |
| 5,324,279 | 6/1994 | Lancaster et al. | 604/391 |
| 5,334,428 | 8/1994 | Dobreski et al. | 428/34.9 |
| 5,342,344 | 8/1994 | Lancaster et al. | 604/387 |
| 5,344,693 | 9/1994 | Sanders | 428/167 |
| 5,453,296 | 9/1995 | Lauritzen et al. | 427/208.6 |
| 5,458,938 | 10/1995 | Nygard et al. | 428/40 |
| 5,487,929 | 1/1996 | Rusincovitch, Jr. et al. | 428/40 |
| 5,514,122 | 5/1996 | Morris et al. | 604/387 |
| 5,518,801 | 5/1996 | Chappell et al. | 428/152 |
| 5,527,112 | 6/1996 | Dais et al. | 383/211 |
| 5,575,747 | 11/1996 | Dais et al. | 493/213 |
| 5,585,178 | 12/1996 | Calhoun et al. | 428/343 |
| 5,589,246 | 12/1996 | Calhoun et al. | 428/120 |

FOREIGN PATENT DOCUMENTS

| | | | |
|---|---|---|---|
| 0 623 332 A1 | 9/1994 | (EP) | A61F/13/15 |
| 0 621 082 A1 | 10/1994 | (EP) | B05C/1/08 |
| 1 315 903 | 4/1963 | (FR) | . |
| 1429312 | 2/1996 | (FR) | . |
| 975783 | 11/1964 | (GB) | . |
| 1069445 | 5/1967 | (GB) | . |
| 3-002292 | 1/1991 | (JP) | A61F/13/56 |
| 7-246216 | 9/1995 | (JP) | A61F/13/56 |
| WO 92/00187 | 1/1992 | (WO) | B32B/3/00 |
| WO 95/11945 | 5/1995 | (WO) | C09J/7/02 |
| WO 95/31225 | 11/1995 | (WO) | A61L/15/58 |
| WO 96/31652 | 10/1996 | (WO) | D21H/27/02 |
| WO 96/41604 | 12/1996 | (WO) | A61F/13/58 |
| WO 97/18276 | 5/1997 | (WO) | C09J/7/02 |

OTHER PUBLICATIONS

Lim, J.H.F., et al., "Statistical Models to Describe the Structure of Porus Ceramic Membranes", Separation Science and Technology, 28 (1–3), pp. 821–854 (1993).

Watson, D.F., "Computing the n–dimensional Delaunay Tessellation with Application To Voronoi Polytopes". The Computer Journal, vol. 24, No. 2, pp. 167–172 (1981).

STORAGE WRAP MATERIAL

CROSS-REFERENCE TO RELATED APPLICATION

This application is a continuation-in-part of commonly-assigned, U.S. patent application Ser. No. 08/584,638, filed Jan. 10, 1996, now U.S. Pat. No. 5,662,758, in the names of Peter W. Hamilton and Kenneth S. McGuire.

FIELD OF THE INVENTION

The present invention relates to sheet-like materials suitable for use in the containment and protection of various items, as well as the preservation of perishable materials such as food items. The present invention further relates to such materials which are suitable for direct contact with such items as a unitary package as well as for use in forming a closure for a semi-enclosed container.

BACKGROUND OF THE INVENTION

Sheet-like materials for use in the containment and protection of various items, as well as the preservation of perishable materials such as food items, are well known in the art. Such materials can be utilized to wrap items individually and/or can be utilized to form a closure for a semi-enclosed container.

One class of such materials in common use today comprises those of polymeric composition formed into a thin, conformable web commonly supplied in rolled form. Common examples of such materials are polyvinyl chloride (PVC), polyvinylidene chloride (PVDC), and polyethylene (PE) sheet materials. These materials exhibit a clinging character on at least one surface due to the properties of the polymeric materials they are formed from and/or additives such as plasticizers, tackifiers, etc., such that they may be folded or wrapped around an item such that they cling to the item and/or to themselves. The clinging character of such materials also permits their use in combination with semi-enclosed rigid, semi-rigid, or flexible containers to provide a fully enclosed container structure. The barrier properties of many such materials, particularly their oxygen, moisture/moisture vapor, and odor barrier properties, provide the desired preservation characteristics for perishable items such as food items and/or items which oxidize or otherwise degrade more rapidly with continued exposure to environmental conditions.

While these materials have achieved a certain level of acceptance, where the material is supplied in the form of a continuous roll in a dispensing carton or apparatus, difficulty is often encountered locating and isolating the current end portion of the rolled web in order to start the dispensing operation. In order to address this issue, a number of methods of identifying and/or isolating the current end of the rolled web have been developed (tabs, colors, end-grasping dispenser features, etc.) which have achieved varying levels of success. Irregardless of the issue of handling the end of the rolled web, the tendency of the material to cling to itself also increases the dispensing force required to unroll the web and tangentially separate the dispensed portion and, if excessive, can lead to a phenomenon known as "roll blocking" wherein the dispensing force to unroll becomes excessive. Roll blocking can also cause excessive dispensing forces which can lead to longitudinal tearing of the web in the roll direction, leading the user to dispense a narrower, unevenly-torn portion of the rolled web. In addition, users frequently encounter situations wherein the material clings to itself prematurely (i.e., before contacting the desired bonding surface), thus necessitating either the manual disengagement of the clinging portion(s) and/or discarding of the material in favor of a new portion.

Another difficulty which may be encountered is the failure of the material to adhere to itself and/or the desired target surface sufficiently to form an airtight seal either from the outset or after a period of handling of the container or wrapped item. If such materials cannot form a seal with barrier properties at least as great as those of the material itself, the full potential of such materials in use as a storage wrap cannot be realized as the seal becomes the weakest link in terms of containerization. Accordingly, some users employ additional securement features such as rubber bands, tapes, etc. Wrinkles in the material where it clings to itself or a target surface can leave small channels in the region between the material and the opposing surface, thereby causing a failure to achieve the desired seal quality for preservation of perishable items. Some users attempt to address seal quality shortcomings by double- or triple-wrapping the desired item to form a tortuous labyrinth seal path of increased length.

Also, because the materials "cling" to themselves and other surfaces, i.e., exhibit an attraction or affinity for the material rather than an adhesive bond, their affinity for a complementary surface is highly dependent upon material characteristics such as chemical composition, electrical conductivity, surface energy, surface finish, etc. Therefore, such materials leave room for improvement both in ease of use as well as ability to form an adequate seal for preservation of perishable items. In many instances, the plasticizers, tackifiers, and other cling additives utilized to provide the cling properties of such materials may also introduce undesirable attributes such as odor to the finished web and/or may introduce environmental concerns.

Another class of materials in common use today comprises thin, conformable webs of various compositions commonly supplied in individual sheet or rolled form. Common examples of such materials include aluminum foil, coated (waxed, etc.) paper, etc. These materials exhibit no adhesive or cling character on either surface, instead relying upon the dead-fold characteristics of the materials they are formed from such that they may be folded or wrapped around an item and retain their folded or wrapped shape. The ability of these materials to maintain their folded or creased shape also permits their use in combination with semi-enclosed rigid, semi-rigid, or flexible containers to provide a fully enclosed container structure. The barrier properties of many such materials, particularly their oxygen, moisture/moisture vapor, and odor barrier properties, provide the desired preservation characteristics for perishable items such as food items and/or items which oxidize or otherwise degrade more rapidly with continued exposure to environmental conditions.

While these materials have achieved a certain level of acceptance, users frequently encounter situations wherein the material fails to remain sufficiently folded and engaged with itself and/or a semi-enclosed container to adequately enclose and preserve the item (i.e., the folds tend to unfold with time or mechanical disturbance), thus necessitating either refolding and external securement of the folded portion(s) and/or discarding of the material in favor of a new portion and re-accomplishing the wrapping process. In some instances, such materials may also be constructed of very thin materials in order to achieve the desired degree of conformability. This may result in the material having insufficient tensile properties to dispense from a roll without longitudinal tearing of the web in the roll direction, leading the user to dispense a narrower, unevenly-torn portion of the rolled web.

Another difficulty which may be encountered is the failure of the material to form an adequate seal where folded either from the outset or after a period of handling of the container or wrapped item. If such materials cannot form a seal with barrier properties at least as great as those of the material itself, the full potential of such materials in use as a storage wrap cannot be realized as the seal becomes the weakest link in terms of containerization. Accordingly, some users undertake to employ additional securement features such as rubber bands, tapes, etc. Wrinkles in the material where it meets itself or a target surface can leave small channels in the region between the material and the opposing surface, thereby causing a failure to achieve the desired seal quality for preservation of perishable items. Some users attempt to address seal quality shortcomings by double- or triple-wrapping the desired item to form a tortuous labyrinth seal path of increased length.

The effective fold radius of these materials is also a factor in determining their suitability for forming an effective seal, as the fold radius of some materials (paper based, etc.) is determined by such material properties as fiber length. A fold radius which is too large will generally render such a material unsuitable for forming an effective seal. In addition, due to the fact that most such dead-fold type materials are opaque, the condition and/or type of items contained in such a packaging system are also obscured from view, necessitating un-wrapping and re-wrapping the items to permit inspection.

Such materials, due to their lack of any adhesive properties, are also difficult to effectively employ in the preservation of perishable items in combination with a semi-enclosed container where the container provides no physical or mechanical engagement features (such as a conventional bowl) around which to fold the material to effect a mechanical labyrinth-type seal between the material and the container. Therefore, such materials leave room for improvement both in ease of use as well as ability to form an adequate seal for preservation of perishable items.

Accordingly, it would be desirable to provide an improved storage wrap material which exhibits convenient, efficient dispensing by a user by having a readily located end portion and a comparatively low unrolling force.

It would also be desirable to provide such a material which is easily handled and manipulated by a user during the enclosure process yet forms an adequate seal with a wide variety of materials and surfaces to effectively preserve perishable items.

It would also be desirable to provide such a material which is capable of being utilized in various modes of item containment and preservation as desired by a user, such as independent use and/or use in combination with a semi-enclosed container, in efficient fashion by substantially reducing if not eliminating the need for double-wrapping and/or additional securement features.

It would further be desirable to provide such materials which are capable of being readily manufactured, stored, and re-used as desirable for both economic and environmental efficiency.

SUMMARY OF THE INVENTION

The present invention provides an improved storage wrap material comprising a sheet of material having a first side and a second side. The first side comprises an active side exhibiting an adhesion peel force after activation by a user which is greater than an adhesion peel force exhibited prior to activation by a user.

The storage wrap material may be activated by different approaches, but in a preferred embodiment the active side is activatible by an externally applied force exerted upon the sheet of material. The force may be an externally applied compressive force exerted in a direction substantially normal to the sheet of material or may be an externally applied tensile force exerted in a direction substantially parallel to the sheet of material.

The active side of the storage wrap material preferably exhibits an adhesion peel force of at least about 1 ounce per linear inch, more preferably between about 1 and about 2.5 ounces per linear inch, after activation by a user. In accordance with the present invention, the storage wrap material is selectively activatible by a user in discrete regions to provide adhesive properties where and when desired. The use of an adhesive or adhesive-like substance on the surface of the material provides an adhesion peel force after activation which is sufficient to form a barrier seal against a target surface at least as great as those of the material and the target surface such that perishable items, such as food items, may be effectively preserved.

The storage wrap materials of the present invention may be utilized to enclose and protect a wide variety of items by various methods of application, including direct application to the desired item, enclosure of the desired item and securement to itself, and/or in combination with a semi-enclosed container.

Such storage wrap materials of the present invention may be advantageously employed in a container system comprising, in combination, the storage wrap material and a semi-enclosed container with at least one opening surrounded by a peripheral edge. The storage wrap material is adhered to the peripheral edge over the opening following activation by a user to convert the semi-enclosed container to a closed container.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

Figure 1:
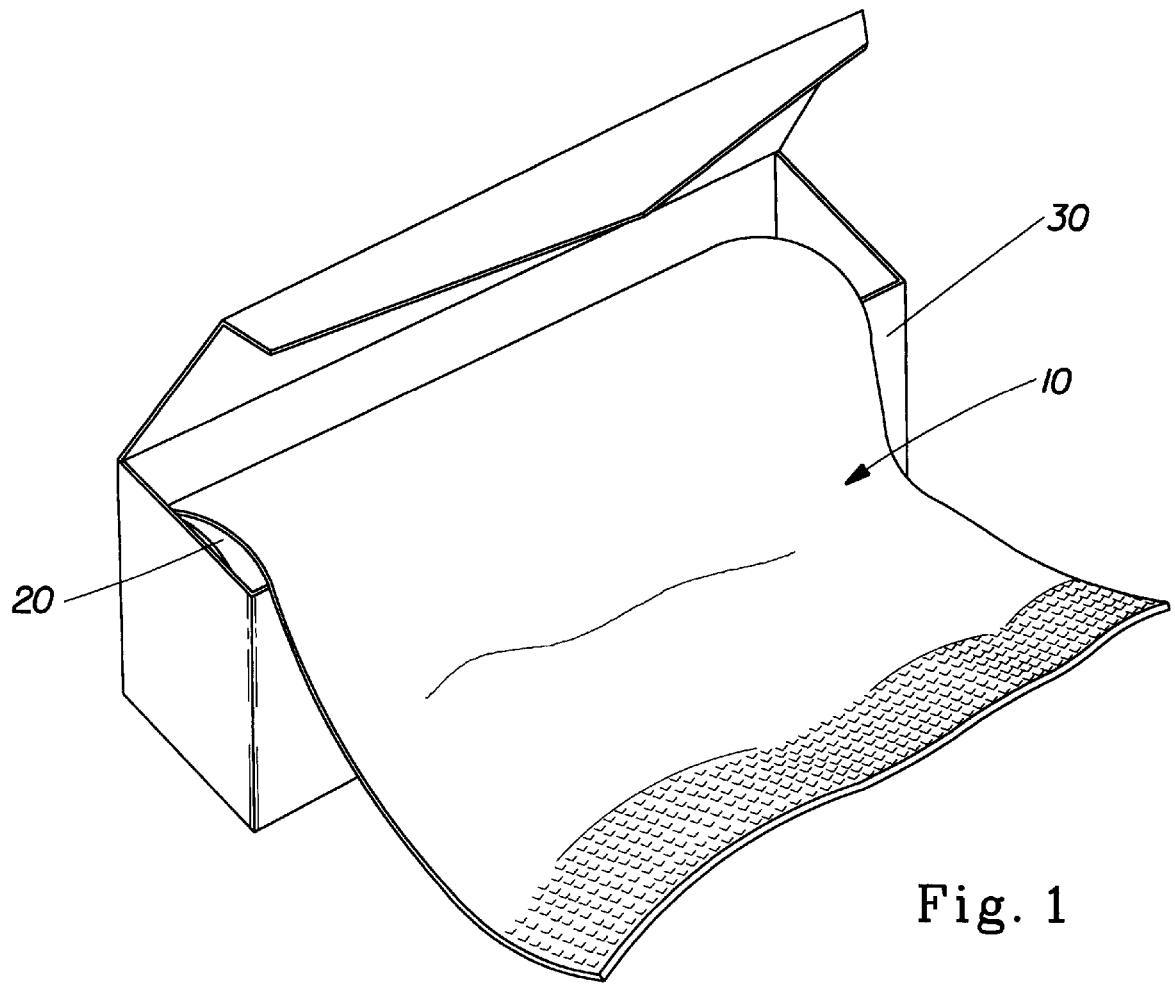
FIG. 1 is a perspective view of the storage wrap material of the present invention provided in roll form.

FIG. 1 depicts a preferred embodiment of a storage wrap material 10 according to the present invention. As shown in FIG. 1, storage wrap material 10 is preferably provided in the form of a web of flexible material which can be wound upon a core to form a roll 20 which is suitable for use in a dispenser or holder such as carton 30. If desired, perforations may be provided to facilitate dispensing of pre-measured dimensions of the material in the event that the dispenser, holder, or container does not include a suitable severing apparatus. Manual severing with sharp implements such as knives and scissors may also be accomplished in order to utilize the material in continuous non-perforated form. In alternative storage and dispensing configurations, the storage wrap material may be provided in the form of discrete, pre-measured sheets of uniform or non-uniform dimensions which may be stacked upon one another in any desired sequence and/or orientation and dispensed from a carton, bag, or any other suitable dispensing apparatus. In another alternative storage and dispensing configuration, the storage wrap material may be provided in the form of a continuous web which is Z-folded or pleated and placed in a dispensing carton.

In accordance with the present invention, storage wrap material 10 exhibits minimal, and preferably no, adhesive or cling properties until activated by a user. This characteristic permits storage wrap 10 to be stored and dispensed in any desired mode without encountering the difficulties of premature clinging or adhering to itself, and without the need for separate release sheets, liners, spacers, or the like. At the same time, when activated at the desired location and at the desired time, the storage wrap material exhibits sufficient adhesive properties to form a bond to most common materials which is sufficiently strong so as to survive handling without failure. The bond between the storage wrap material and a target surface is also sufficient to provide a barrier seal against transmission of oxygen, moisture/moisture vapor, odor, etc. such that perishable items may be satisfactorily enclosed and preserved to the extent of the barrier properties of the material itself.

Although storage wrap material may be provided with two active sides or surfaces, if desired for particular applications, in accordance with the present invention it is presently preferred to provide storage wrap material with only one active side and one inactive or inert side.

The active side of the storage wrap material may be selectively activated by a user to provide activated regions where desired to provide selective adhesion of the material to a target surface. The target surface may comprise a separate surface or material, such as a container or an item or items to be wrapped, or may comprise another portion of the storage wrap material itself. Selective activation results in the generation of only so much active area with adhesive properties as is needed, i.e., all remaining portions of the storage wrap material remain inactive or inert. The storage wrap material is therefore capable of forming discrete inactive and active regions on the same side of the material in addition to the ability to have an active side and an inactive side.

Various means of activation are envisioned as being within the scope of the present invention, such as compression, extension, thermal activation, etc. However, in terms of providing the user with the desired degree of control over the activation process the compression activation method is presently preferred.

Regardless of the manner of activation, storage wrap materials of the present invention will exhibit an adhesive, adherent, or tacking character as opposed to merely a clinging or affinity character. Accordingly, such storage wrap materials will form a bond or seal when in contact with itself or another target surface as opposed to merely being attracted to such surface. While a number of approaches such as the use of selectively adherent materials may be utilized to provide the desired adhesive properties, a presently preferred approach is to utilize a pressure-sensitive adhesive. When designing storage wrap materials in accordance with the present invention, it may be desirable to tailor the particular choice of adhesive agent so as to provide either a permanent bond or a releasable bond as desired for a particular application. Where a permanent bond is desired, opening of the wrap or enclosed container for access to the item(s) therein requires destruction of the storage wrap and/or the container. Releasable bonds, on the other hand, provide access to the wrapped item(s) by permitting separation of the wrap from itself or the container at the bond site without destruction. Moreover, depending upon the activation mechanism employed in the design of the storage wrap material, the releasable bond may additionally be refastenable if sufficient adhesive character remains after the initial activation/bonding/release cycle.

Several physical characteristics or properties are believed to be important in the design and construction of a suitable storage wrap material in accordance with the present invention.

In order to accommodate a wide range of items to be wrapped/packaged in terms of shape and size, as well as a wide range of container shapes when utilized in combination with a semi-enclosed container, the storage wrap material is preferably sufficiently flexible to conform readily to any desired surface. At the same time, the memory or resiliency of the material must be sufficiently small that it does not exert undue restorative forces which would tend to cause the material to break contact with the container/item/target surface and thus become prematurely unsecured or unsealed over time. While design of the storage wrap material for the intended application will require a balancing of the various physical properties, as a general proposition it is presently preferred for a wide variety of applications to select a material having greater plasticity than elasticity.

Another property which has been found to be important in designing storage wrap materials in accordance with the present invention is the degree of adhesion that they exhibit after activation by a user. More particularly, the storage wrap materials of the present invention exhibit an adhesion sufficient to survive the likely degree of handling the wrapped item or enclosed container is likely to encounter in use while maintaining the desired level of sealing engagement with the item, with itself, or with the accompanying semi-enclosed container such that preservation of perishable items is ensured.

One way to measure or quantify this adhesion property is in terms of an adhesion peel force value which is preferably measured by Pressure Sensitive Tape Council Method PSTC-1. A 12 inch (30.5 cm) long by 1 inch (2.5 cm) wide strip of film is rolled once against a smooth stainless steel surface at a rate of 12 inches (30.5 cm) per minute using a 4.5 pound (2.04 kg) roller and then tested as having a peak adhesion peel force value ranging from about 1 to about 50 ounces/inch (0.012 to 0.600 kg/cm), more preferably from about 1 to about 2.5 ounces/inch (0.012 to 0.027 kg/cm) of strip width. In general, minimum adhesion which maintains a seal is desired for a storage wrap, so that the wrap is easily peeled open for access to the stored item(s).

In a preferred embodiment, the improved storage wrap material of the present invention is a substantially clingless wrap material in contrast to typical commercially-available storage wrap materials. As discussed above, such materials exhibit "cling" properties on a constant basis, such that they cling to themselves and to other surfaces whenever brought into proximity with them, whether desirable or not. Such materials often incorporate resins, additives, tackifiers, or other materials to achieve the target level of cling. Suitable methods of measuring and quantifying this cling property are described in ASTM test methods D5458-95 and D3354-89. Test method D5458-95 is useful for measuring cling between two layers of film in both stretched and unstretched conditions, and utilizes a 1 inch wide film strip adhered to a flat film attached to an inclined surface. The force required to remove the film strip from the flat film is measured. Test method D3354-89 is useful for measuring the degree of blocking (unwanted adhesion) existing between overlapping layers of plastic film. Film-to-film adhesion is expressed as a blocking load in grams which will cause two layers of polyethylene film to separate with an area of contact of 100 square centimeters.

Substantially clingless wrap materials in accordance with the present invention can be produced by proper selection of materials including the avoidance of any significant amount of materials known in the art as "cling additives", including those of the types described above. Further, additional materials or additives can be incorporated as needed to further reduce, if not eliminate, the tendency of such materials to cling to themselves and other surfaces. Such materials would include anti-static agents, etc.

The improved storage wrap materials of the present invention may take many forms and may be manufactured by a variety of different approaches. One design category that can provide the required properties incorporates the use of standoffs to prevent an adhesive layer from making contact with external surfaces before intended to do so. Through user activation, the standoffs are designed to be deformable, removable, repositionable, or frangible in order to expose the adhesive, when intended, to the target surface. One particular approach within that design category which is believed to be presently preferred is to form a three-dimensional polymeric film structure with a layer of pressure-sensitive adhesive protected from contact with other surfaces by integrally-formed deformable protrusions or stand-offs. To activate the material, once the material is positioned over the desired target surface (which may be another portion of itself) the user exerts a pressure on the desired location of the material to collapse the protrusions and bring the adhesive into engagement with the target surface to form the desired bond. Such materials are described in greater detail in commonly-assigned, co-pending U.S. patent application Ser. No. 08/584,638, filed Jan. 10, 1996 in the names of Peter W. Hamilton and Kenneth S. McGuire, entitled "Composite Material Releasably Sealable To A Target Surface When Pressed There-against and Method of Making", now U.S. Pat. No. 5,662,758, the disclosure of which is hereby incorporated herein by reference.

If such a three-dimensional structure is used as a storage wrap in accordance with the present invention, for example, the external contact surfaces may be either compliant or rigid and planar or non-planar. Having the three dimensional structure deform is preferred for use with a rigid target surface. If the substance is adhesive and the objective is releasable adherence to a target surface after deformation of the structure, then degree of adhesion is important. Inversion of protrusions, especially those made of HDPE, minimizes protrusion spring back so that higher adhesion isn't necessary in order to prevent the failure of relatively weak seals. In this embodiment it is desired that the protrusion remain "dead" or non-resilient after being inverted or crushed; however, a resilient protrusion could be used, for example, where it is intended for the bond to be permanent, where aggressive adhesive overcomes spring back. Also, a resilient protrusion may be desirable where repeat use of the material is intended.

Figure 2:
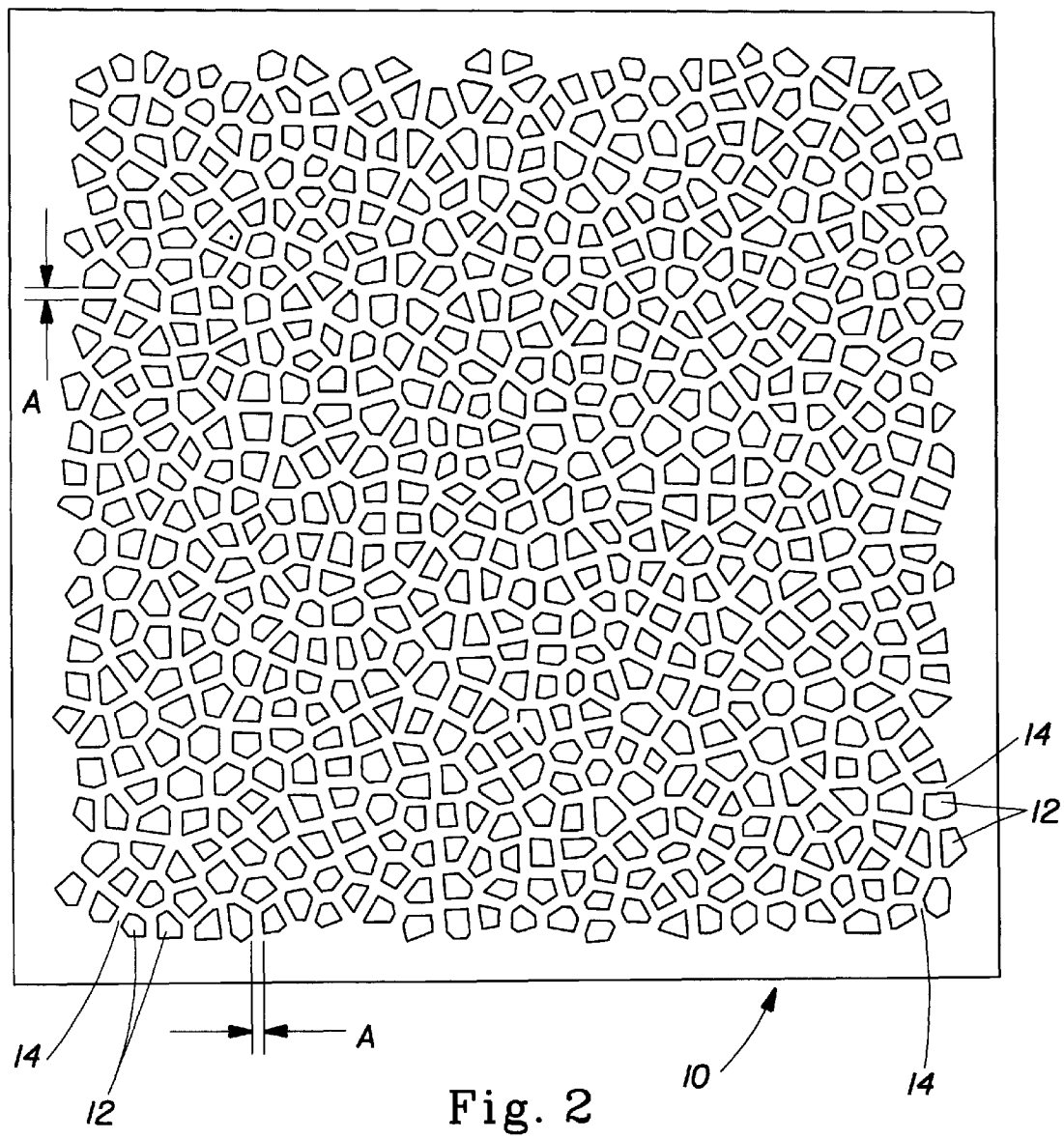
FIG. 2 is a plan view of a preferred embodiment of a three-dimensional, nesting-resistant sheet material suitable for use as a storage wrap material in accordance with the present invention.
Figure 3:
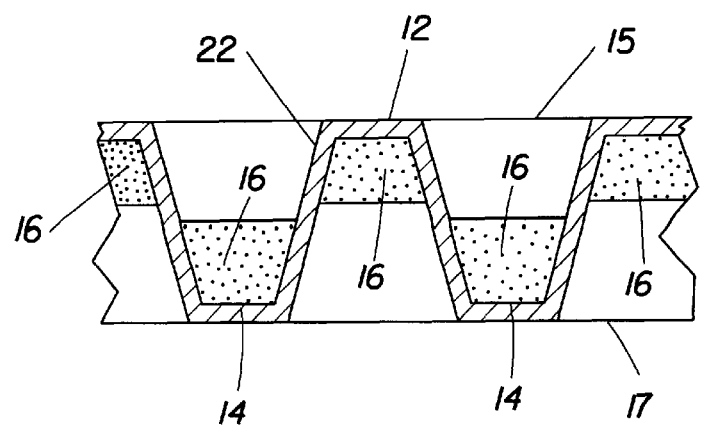
FIG. 3 is a partial elevational sectional view of the sheet material of FIG. 2, wherein a substance is included within the three-dimensional structure of the web.

FIGS. 2–3 illustrates a typical storage wrap material 10 constructed in accordance with the aforementioned Hamilton et al. application which is suitable for use as a storage wrap material of the present invention. In a preferred embodiment, the three-dimensional protrusions depicted in FIGS. 2–3 may be formed in an amorphous pattern of two-dimensional geometrical shapes such that the sheet of material resists nesting of superimposed layers such as would be encountered in a roll of product. Such three-dimensional, nesting-resistant materials and patterns are described in greater detail in commonly-assigned, co-pending, concurrently-filed U.S. patent application Ser. No. 08/745,339, Attorney's Docket No. Case 6356, filed Nov. 8, 1996 in the names of Kenneth S. McGuire, Richard Tweddell, III and Peter W. Hamilton, entitled "Three-Dimensional, Nesting-Resistant Sheet Materials and Method and Apparatus for Making Same", the disclosure of which is hereby incorporated herein by reference.

When the material is formed into an elongated web with the intention of winding it upon a mandrel or upon itself (core-less roll) for purposes of compact storage, in accordance with the present invention the web exhibits the non-uniform pattern at least in the direction of rolling, and most preferably in both the rolling direction and the cross-rolling direction. While an infinitely non-repeating pattern may be desirable for certain applications, at a minimum the materials of the present invention will exhibit a non-uniform pattern property for a web distance at least as great as the maximum intended roll circumference of a roll of product.

In order to provide the greatest degree of nesting-resistance, the three-dimensional, nesting-resistant sheet materials of the present invention preferably exhibit a two-dimensional pattern of three-dimensional protrusions which is substantially amorphous in nature. As utilized herein, the term "amorphous" refers to a pattern which exhibits no readily perceptible organization, regularity, or orientation of constituent elements. This definition of the term "amorphous" is generally in accordance with the ordinary meaning of the term as evidenced by the corresponding definition in *Webster's Ninth New Collegiate Dictionary*. In such a pattern, the orientation and arrangement of one element with regard to a neighboring element bear no predictable relationship to that of the next succeeding element(s) beyond.

By way of contrast, the term "array" is utilized herein to refer to patterns of constituent elements which exhibit a regular, ordered grouping or arrangement. This definition of the term "array" is likewise generally in accordance with the ordinary meaning of the term as evidenced by the corresponding definition in Webster's Ninth New Collegiate Dictionary. In such an array pattern, the orientation and arrangement of one element with regard to a neighboring element bear a predictable relationship to that of the next succeeding element(s) beyond.

The degree to which order is present in an array pattern of three-dimensional protrusions bears a direct relationship to the degree of nestability exhibited by the web. For example, in a highly-ordered array pattern of uniformly-sized and shaped hollow protrusions in a close-packed hexagonal array, each protrusion is literally a repeat of any other protrusion. Nesting of regions of such a web, if not in fact the entire web, can be achieved with a web alignment shift between superimposed webs or web portions of no more than one protrusion-spacing in any given direction. Lesser degrees of order may demonstrate less nesting tendency, although any degree of order is believed to provide some degree of nestability. Accordingly, an amorphous, non-ordered pattern of protrusions would therefore exhibit the greatest possible degree of nesting-resistance.

While it is presently preferred that the entire surface of a web in accordance with the present invention exhibit such an amorphous pattern, under some circumstances it may be desirable for less than the entire surface of such a web to exhibit such a pattern. For example, a comparatively small portion of the web may exhibit some regular pattern of protrusions or may in fact be free of protrusions so as to present a generally planar surface. In addition, wherein the sheet material is to be formed as a comparatively large sheet of material and/or as an elongated continuous web to be folded or wound upon itself, manufacturing constraints may require that the amorphous pattern itself be repeated periodically within the web. Although any pattern repetition within the web allows some possibility of nesting occurring, such a possibility only exists when precise alignment of superimposed webs or web portions occurs with such webs or web portions representing exactly one repeat of the pattern (or an integer number of repeats for a continuous wound or folded web). This contrasts with the nesting character of webs formed of uniformly-shaped protrusions in an array pattern wherein each protrusion is a repeat of the adjacent protrusions such that the repeat distance is a single protrusion spacing. In such a configuration, alignment for nesting would occur if web alignment occurs with a shift of no more than one protrusion-spacing.

In a web with an amorphous pattern of three-dimensional protrusions, any selection of an adjacent plurality of protrusions will be unique within the scope of the pattern, even though under some circumstances it is conceivable that a given individual protrusion may possibly not be unique within the scope of the pattern. By utilizing an amorphous pattern, the three-dimensional sheet of material (in the case of a sheet having hollow, three-dimensional protrusions) will not nest unless precise superposition of sheets of material having the same amorphous pattern occurs.

Three-dimensional sheet materials having a two-dimensional pattern of three-dimensional protrusions which is substantially amorphous in nature are also believed to exhibit "isomorphism". As utilized herein, the terms "isomorphism" and its root "isomorphic" are utilized to refer to substantial uniformity in geometrical and structural properties for a given circumscribed area wherever such an area is delineated within the pattern. This definition of the term "isomorphic" is generally in accordance with the ordinary meaning of the term as evidenced by the corresponding definition in Webster's Ninth New Collegiate Dictionary. By way of example, a prescribed area comprising a statistically-significant number of protrusions with regard to the entire amorphous pattern would yield statistically substantially equivalent values for such web properties as protrusion area, number density of protrusions, total protrusion wall length, etc. Such a correlation is believed desirable with respect to physical, structural web properties when uniformity is desired across the web surface, and particularly so with regard to web properties measured normal to the plane of the web such as crush-resistance of protrusions, etc.

Utilization of an amorphous pattern of three-dimensional protrusions has other advantages as well. For example, it has been observed that three-dimensional sheet materials formed from a material which is initially isotropic within the plane of the material remain generally isotropic with respect to physical web properties in directions within the plane of the material. As utilized herein, the term "isotropic" is utilized to refer to web properties which are exhibited to substantially equal degrees in all directions within the plane of the material. This definition of the term "isotropic" is likewise generally in accordance with the ordinary meaning of the term as evidenced by the corresponding definition in Webster's Ninth New Collegiate Dictionary. Without wishing to be bound by theory, this is presently believed to be due to the non-ordered, non-oriented arrangement of the three-dimensional protrusions within the amorphous pattern. Conversely, directional web materials exhibiting web properties which vary by web direction will typically exhibit such properties in similar fashion following the introduction of the amorphous pattern upon the material. By way of example, such a sheet of material could exhibit substantially uniform tensile properties in any direction within the plane of the material if the starting material was isotropic in tensile properties.

Such an amorphous pattern in the physical sense translates into a statistically equivalent number of protrusions per unit length measure encountered by a line drawn in any given direction outwardly as a ray from any given point within the pattern. Other statistically equivalent parameters could include number of protrusion walls, average protrusion area, average total space between protrusions, etc. Statistical equivalence in terms of structural geometrical features with regard to directions in the plane of the web is believed to translate into statistical equivalence in terms of directional web properties.

Revisiting the array concept to highlight the distinction between arrays and amorphous patterns, since an array is by definition "ordered" in the physical sense it would exhibit some regularity in the size, shape, spacing, and/or orientation of protrusions. Accordingly, a line or ray drawn from a given point in the pattern would yield statistically different values depending upon the direction in which the ray extends for such parameters as number of protrusion walls, average protrusion area, average total space between protrusions, etc. with a corresponding variation in directional web properties.

Within the preferred amorphous pattern, protrusions will preferably be non-uniform with regard to their size, shape, orientation with respect to the web, and spacing between adjacent protrusion centers. Without wishing to be bound by theory, differences in center-to-center spacing of adjacent protrusions are believed to play an important role in reducing the likelihood of nesting occurring in the face-to-back nesting scenario. Differences in center-to-center spacing of protrusions within the pattern result in the physical sense in the spaces between protrusions being located in different spatial locations with respect to the overall web. Accordingly, the likelihood of a "match" occurring between superimposed portions of one or more webs in terms of protrusions/space locations is quite low. Further, the likelihood of a "match" occurring between a plurality of adjacent protrusions/spaces on superimposed webs or web portions is even lower due to the amorphous nature of the protrusion pattern.

In a completely amorphous pattern, as would be presently preferred, the center-to-center spacing is random, at least within a designer-specified bounded range, such that there is an equal likelihood of the nearest neighbor to a given protrusion occurring at any given angular position within the plane of the web. Other physical geometrical characteristics of the web are also preferably random, or at least non-uniform, within the boundary conditions of the pattern, such as the number of sides of the protrusions, angles included within each protrusion, size of the protrusions, etc. However, while it is possible and in some circumstances desirable to have the spacing between adjacent protrusions be non-uniform and/or random, the selection of polygon shapes which are capable of interlocking together makes a uniform spacing between adjacent protrusions possible. This is particularly useful for some applications of the three-dimensional, nesting-resistant sheet materials of the present invention, as will be discussed hereafter.

A sheet or web of material can be intentionally created with a plurality of amorphous areas within the same sheet or web, even to the point of replication of the same amorphous pattern in two or more such regions. The designer may purposely separate amorphous regions with a regular defined, non-amorphous pattern or array, or even a "blank" region with no protrusions at all, or any combination thereof. The formations contained within a non-amorphous area can be of any number density, height or shape. Further, the shape and dimensions of the non-amorphous region itself can be customized as desired. Additional examples of formation shapes, but not intended to be exhaustive, are: wedges emanating from a point; truncated wedges; polygons; circles; curvilinear shapes; or combinations thereof.

Additionally, a single amorphous region may fully envelop or circumscribe one or more non-amorphous areas. An example is a single, continuous amorphous region with non-amorphous patterns fully enclosed near the center of the sheet or web. Such imbedded patterns may communicate brand name, the manufacturer, instructions, material side or face indication, other information or simply be decorative in nature.

Multiple non-amorphous regions may be abutted or overlapped in a substantially contiguous manner to substantially divide one amorphous pattern into multiple regions or to separate multiple amorphous regions that were never part of a greater single amorphous region beforehand.

From the foregoing discussion it would be apparent that the utilization of an amorphous pattern of three-dimensional protrusions enables the fabrication of webs having the advantages of an array pattern, for example, statistical uniformity in web properties on an area/location basis, without the key disadvantages of using an array in such applications, namely nestability and anisotropism.

Webs according to the present invention may have protrusions formed of virtually any three-dimensional shape, and accordingly need not be all of a convex polygonal shape. However, it is presently preferred to form the protrusions in the shape of substantially-equal-height frustums having convex polygonal bases in the plane of one surface of the material and having interlocking, adjacent parallel sidewalls. For other applications, however, the protrusions need not necessarily be of polygonal shape.

As used herein, the term "polygon" (and the adjective form "polygonal") is utilized to refer to a two-dimensional geometrical figure with three or more sides, since a polygon with one or two sides would define a line. Accordingly, triangles, quadrilaterals, pentagons, hexagons, etc. are included within the term "polygon", as would curvilinear shapes such as circles, ellipses, etc. which would have an infinite number of sides.

When designing a three-dimensional structure, the desired physical properties of the resulting structure will dictate the size, geometrical shape, and spacing of the three-dimensional topographical features as well as the choice of materials and forming techniques. For example, deformable three-dimensional protrusions will typically exhibit varying degrees of deformabilty, particularly crushability, depending upon their cross-sectional shape and average equivalent diameter. The bending modulus and/or flexibility of the overall web will depend upon the relative proportion of two-dimensional material between three-dimensional protrusions.

When describing properties of three-dimensional structures of non-uniform, particularly non-circular, shapes and non-uniform spacing, it is often useful to utilize "average" quantities and/or "equivalent" quantities. For example, in terms of characterizing linear distance relationships between three-dimensional protrusions in a two-dimensional pattern, where spacings on a center-to-center basis or on an individual spacing basis, an "average" spacing term may be useful to characterize the resulting structure. Other quantities that could be described in terms of averages would include the proportion of surface area occupied by protrusions, protrusion area, protrusion circumference, protrusion diameter, etc. For other dimensions such as protrusion circumference and protrusion diameter, an approximation can be made for protrusions which are non-circular by constructing a hypothetical equivalent diameter as is often done in hydraulic contexts.

The three-dimensional shape of individual protrusions is believed to play a role in determining both the physical properties of individual protrusions as well as overall web properties. Of particular interest for certain applications is crush resistance of protrusions (i.e., their ability to resist a deformation by crushing and/or inverting in a direction substantially perpendicular to the plane of the material). Without wishing to be bound by theory, it is presently believed that the crush resistance of a given protrusion depends upon the crush strengths of the individual panel segments which define each facet along the perimeter of the protrusion. The panel segment with the lowest crush strength limits the crush strength of the protrusion, much as the weakest link defines the strength of a length of chain.

Buckling strengths of individual panels can be increased by introducing curvature to the panel in a plane perpendicular to the crush direction, with buckling strength increasing with decreasing radius of curvature. Buckling strengths of individual panels may also be increased by decreasing the width of the panel for a constant height (i.e., decreasing the aspect ratio). In the case of non-curvilinear protrusions having a finite number of sides of substantially planar shape, application of these principles suggests that protrusions will exhibit generally greater crush resistance as the equality in side length and included angles increases by minimizing the "weakest link" effect. Accordingly, a protrusion with one side substantially longer than the others will be limited in crush strength by the buckling behavior of that longest side. Therefore, crush strength for a given perimeter and given wall thickness would be greater for a protrusion having a greater number of smaller sides and would maximize its crush resistance by having the sides of substantially similar dimensions to minimize the weakest link effect.

It should be noted that the foregoing discussion assumes geometric replication of three-dimensional structures from a forming structure of geometrically-sound shapes. "Real world" effects such as curvature, degree of moldability, radius of corners, etc. should be taken into account with regard to ultimately exhibited physical properties.

The use of an interlocking network of frustums provides some sense of uniformity to the overall web structure, which aids in the control and design of overall web properties such as web stretch, tensile strength, roll profile and thickness, etc., while maintaining the desired degree of amorphousness in the pattern. In addition, when utilized as a base structure for application of an adhesive or other active substance as described in the above-referenced and incorporated commonly-assigned, co-pending U.S. patent application Ser. No. 08/584,638, the use of an interlocking polygonal base pattern for the protrusions provides a controllable width and spacing of the valleys between the protrusions so that the area available for contact of the active agent with a target surface may be tailored. The use of external polygonal bases from which the sides of the frustums extend upwardly also add a degree of predictability and uniformity to the collapse of the protrusions under compressive forces and also improves the release properties of the formed material from the corresponding forming structure.

The use of polygons having a finite number of sides in the amorphous pattern arranged in an interlocking relationship also provides an advantage over structures employing circular or nearly-circular shapes. Patterns such as arrays employing closely-packed circles are limited in terms of the amount of area the circles can occupy relative to the non-circled area between adjacent circles. More specifically, even in a pattern where adjacent circles touch at their point of tangency there will still be a given amount of space "trapped" at the "corners" between consecutive points of tangency. Accordingly, even amorphous patterns of circular shapes are limited in terms of how little non-circle area can be designed into the structure. Conversely, interlocking polygonal shapes with finite numbers of sides (i.e., no shapes with curvilinear sides) can be designed so as to pack closely together and in the limiting sense can be packed such that adjacent sides of adjacent polygons can be in contact along their entire length such that there is no "trapped" free space between corners. Such patterns therefore open up the entire possible range of polygon area from nearly 0% to nearly 100%, which may be particularly desirable for certain applications where the low end of free space becomes important for functionality.

Any suitable method may be utilized to design the interlocking polygonal arrangement of hollow frustums which provides suitable design capability in terms of desirable protrusion size, shape, taper, spacing, repeat distance, etc. Even manual methods of design may be utilized. Such pattern may be imparted to the starting web material in any suitable fashion, including manual methods and methods of individually custom-forming the protrusions.

However, in accordance with the present invention, an expeditious method of designing and forming such protrusions has been developed which permits the precise tailoring of desirable protrusion size, shape, taper, and spacing within an amorphous pattern, repeat distance of the amorphous pattern, etc. as well as the continuous formation of webs containing such protrusions in an automated process.

A totally random pattern of three-dimensional hollow protrusions in a web would, in theory, never exhibit face-to-back nesting since the shape and alignment of each frustum would be unique. However, the design of such a totally random pattern would be very time-consuming and complex proposition, as would be the method of manufacturing a suitable forming structure. In accordance with the present invention, the non-nesting attributes may be obtained by designing patterns or structures where the relationship of adjacent cells or structures to one another is specified, as is the overall geometrical character of the cells or structures, but wherein the precise size, shape, and orientation of the cells or structures is non-uniform and non-repeating. The term "non-repeating", as utilized herein, is intended to refer to patterns or structures where an identical structure or shape is not present at any two locations within a defined area of interest. While there may be more than one protrusion of a given size and shape within the pattern or area of interest, the presence of other protrusions around them of non-uniform size and shape virtually eliminates the possibility of an identical grouping of protrusions being present at multiple locations. Said differently, the pattern of protrusions is non-uniform throughout the area of interest such that no grouping of protrusions within the overall pattern will be the same as any other like grouping of protrusions. The beam strength of the three-dimensional sheet material will prevent significant nesting of any region of material surrounding a given protrusion even in the event that that protrusion finds itself superimposed over a single matching depression since the protrusions surrounding the single protrusion of interest will differ in size, shape, and resultant center-to-center spacing from those surrounding the other protrusion/depression.

Professor Davies of the University of Manchester has been studying porous cellular ceramic membranes and, more particularly, has been generating analytical models of such membranes to permit mathematical modeling to simulate real-world performance. This work was described in greater detail in a publication entitled "Porous cellular ceramic membranes: a stochastic model to describe the structure of an anodic oxide membrane", authored by J. Broughton and G. A. Davies, which appeared in the *Journal of Membrane Science*, Vol. 106 (1995), at pp. 89–101, the disclosure of which is hereby incorporated herein by reference. Other related mathematical modeling techniques are described in greater detail in "Computing the n-dimensional Delaunay tessellation with application to Voronoi polytopes", authored by D. F. Watson, which appeared in *The Computer Journal*, Vol. 24, No. 2 (1981), at pp. 167–172, and "Statistical Models to Describe the Structure of Porous Ceramic Membranes", authored by J. F. F. Lim, X. Jia, R. Jafferali, and G. A. Davies, which appeared in *Separation Science and Technology*, 28(1–3) (1993) at pp. 821–854, the disclosures of both of which are hereby incorporated herein by reference.

As part of this work, Professor Davies developed a two-dimensional polygonal pattern based upon a constrained Voronoi tessellation of 2-space. In such a method, again with reference to the above-identified publication, nucleation points are placed in random positions in a bounded (pre-determined) plane which are equal in number to the number of polygons desired in the finished pattern. A computer program "grows" each point as a circle simultaneously and radially from each nucleation point at equal rates. As growth fronts from neighboring nucleation points meet, growth stops and a boundary line is formed. These boundary lines each form the edge of a polygon, with vertices formed by intersections of boundary lines.

While this theoretical background is useful in understanding how such patterns may be generated and the properties of such patterns, there remains the issue of performing the above numerical repetitions step-wise to propagate the nucleation points outwardly throughout the desired field of interest to completion. Accordingly, to expeditiously carry out this process a computer program is preferably written to perform these calculations given the appropriate boundary conditions and input parameters and deliver the desired output.

The first step in generating a pattern for making a three-dimensional forming structure is to establish the dimensions of the desired forming structure. For example, if it is desired to construct a forming structure 8 inches wide and 10 inches long, for optionally forming into a drum or belt as well as a plate, then an X-Y coordinate system is established with the maximum X dimension ($X_{Max}$) being 8 inches and the maximum Y dimension ($Y_{Max}$) being 10 inches (or vice-versa).

After the coordinate system and maximum dimensions are specified, the next step is to determine the number of "nucleation points" which will become polygons corresponding to the number of protrusions desired within the defined boundaries of the forming structure. This number is an integer between 0 and infinity, and should be selected with regard to the average size and spacing of the polygons desired in the finished pattern. Larger numbers correspond to smaller polygons, and vice-versa. A useful approach to determining the appropriate number of nucleation points or polygons is to compute the number of polygons of an artificial, hypothetical, uniform size and shape that would be required to fill the desired forming structure. Assuming common units of measurement, the forming structure area (length times width) divided by the square of the sum of the polygon diameter and the spacing between polygons will yield the desired numerical value N (rounded to the nearest integer). This formula in equation form would be:

$$N = \frac{X_{Max} Y_{Max}}{(\text{polygon size} + \text{polygon spacing})^2}$$

A random number generator is required for the next step. Any suitable random number generator known to those skilled in the art may be utilized, including those requiring a "seed number" or utilizing an objectively determined starting value such as chronological time. Many random number generators operate to provide a number between zero and one (0–1), and the discussion hereafter assumes the use of such a generator. A generator with differing output may also be utilized if the result is converted to some number between zero and one or if appropriate conversion factors are utilized.

A computer program is written to run the random number generator the desired number of iterations to generate as many random numbers as is required to equal twice the desired number of "nucleation points" calculated above. As the numbers are generated, alternate numbers are multiplied by either the maximum X dimension or the maximum Y dimension to generate random pairs of X and Y coordinates all having X values between zero and the maximum X dimension and Y values between zero and the maximum Y dimension. These values are then stored as pairs of (X,Y) coordinates equal in number to the number of "nucleation points".

If the method described in the preceding paragraph is utilized to generate a resulting pattern, the pattern will be truly random. This truly random pattern will, by its nature, have a large distribution of polygon sizes and shapes which may be undesirable in some instances. For example, a large distribution of polygon sizes may lead to large variations in web properties in various regions of the web and may lead to difficulties in forming the web depending upon the formation method selected. In order to provide some degree of control over the degree of randomness associated with the generation of "nucleation point" locations, a control factor or "constraint" is chosen and referred to hereafter as β (beta). The constraint limits the proximity of neighboring nucleation point locations through the introduction of an exclusion distance, E, which represents the minimum distance between any two adjacent nucleation points. The exclusion distance E is computed as follows:

$$E = \frac{2\beta}{\sqrt{\lambda\pi}}$$

where λ (lambda) is the number density of points (points per unit area) and β ranges from 0 to 1.

To implement the control of the "degree of randomness", the first nucleation point is placed as described above. β is then selected, and E is calculated from the above equation. Note that β, and thus E, will remain constant throughout the placement of nucleation points. For every subsequent nucleation point (X,Y) coordinate that is generated, the distance from this point is computed to every other nucleation point that has already been placed. If this distance is less than E for any point, the newly-generated (XY) coordinates are deleted and a new set is generated. This process is repeated until all N points have been successfully placed. If β=0, then the exclusion distance is zero, and the pattern will be truly random. If β=1, the exclusion distance is equal to the nearest neighbor distance for a hexagonally close-packed array. Selecting β between 0 and 1 allows control over the "degree of randomness" between these two extremes.

Once the complete set of nucleation points are computed and stored, a Delaunay triangulation is performed as the precursor step to generating the finished polygonal pattern. The use of a Delaunay triangulation in this process constitutes a simpler but mathematically equivalent alternative to iteratively "growing" the polygons from the nucleation points simultaneously as circles, as described in the theoretical model above. The theme behind performing the triangulation is to generate sets of three nucleation points forming triangles, such that a circle constructed to pass through those three points will not include any other nucleation points within the circle. To perform the Delaunay triangulation, a computer program is written to assemble every possible combination of three nucleation points, with each nucleation point being assigned a unique number (integer) merely for identification purposes. The radius and center point coordinates are then calculated for a circle passing through each set of three triangularly-arranged points. The coordinate locations of each nucleation point not used to define the particular triangle are then compared with the coordinates of the circle (radius and center point) to determine whether any of the other nucleation points fall within the circle of the three points of interest. If the constructed circle for those three points passes the test (no other nucleation points falling within the circle), then the three point numbers, their X and Y coordinates, the radius of the circle, and the X and Y coordinates of the circle center are stored. If the constructed circle for those three points fails the test, no results are saved and the calculation progresses to the next set of three points.

Once the Delaunay triangulation has been completed, a Voronoi tessellation of 2-space is then performed to generate the finished polygons. To accomplish the tessellation, each nucleation point saved as being a vertex of a Delaunay triangle forms the center of a polygon. The outline of the polygon is then constructed by sequentially connecting the center points of the circumscribed circles of each of the Delaunay triangles, which include that vertex, sequentially in clockwise fashion. Saving these circle center points in a repetitive order such as clockwise enables the coordinates of the vertices of each polygon to be stored sequentially throughout the field of nucleation points. In generating the polygons, a comparison is made such that any triangle vertices at the boundaries of the pattern are omitted from the calculation since they will not define a complete polygon.

Once a finished pattern of interlocking polygonal two-dimensional shapes is generated, in accordance with the present invention such a network of interlocking shapes is utilized as the design for one web surface of a web of material with the pattern defining the shapes of the bases of the three-dimensional, hollow protrusions formed from the initially planar web of starting material. In order to accomplish this formation of protrusions from an initially planar web of starting material, a suitable forming structure comprising a negative of the desired finished three-dimensional structure is created which the starting material is caused to conform to by exerting suitable forces sufficient to permanently deform the starting material.

From the completed data file of polygon vertex coordinates, a physical output such as a line drawing may be made of the finished pattern of polygons. This pattern may be utilized in conventional fashion as the input pattern for a metal screen etching process to form a three-dimensional forming structure suitable for forming the materials of the present invention. If a greater spacing between the polygons is desired, a computer program can be written to add one or more parallel lines to each polygon side to increase their width (and hence decrease the size of the polygons a corresponding amount).

Preferably, the computer program described above provides as its output a computer graphic (.TIFF) file. From this data file, a photographic negative can be made for use in a photoetching process to etch negative impressions into a base material to correspond to the desired frustum polygonal shapes in the finished web of material. Alternatively, depending upon the desired process of generating the negative forming structure for forming the finished web, it may be desirable to tailor the output of the computer program to deliver coordinate points, etc. of the polygonal recesses, such as would prove useful if a mechanical process were to be utilized. In addition, if it were desirable to form a male pattern the computer output could be tailored to provide the desired information to the forming apparatus to the extent it may differ than for a negative (female) pattern.

To provide further illustration of the effect of increasing levels of constraint obtained by various values of β, an exemplary β value of 0.25 (i.e., in the lower end of the range of 0 to 1) yields a much greater variation in the center-to-center spacing of the nucleation points and thus the resulting polygons than does an exemplary β value of 0.75 (i.e., near the higher end of the range of 0 to 1). Such degree of variation in center-to-center spacing also in the geometrical sense translates into a corresponding degree of variation in number of sides in the resulting polygons as well as polygon size, the effects of which were discussed above. In order to produce the desired level of amorphousness in the resulting pattern of polygons, the value presently preferred for β is 0.75, but this value may of course be tailored as required to suit a particular application.

The polygon area distribution decreases as the constraint (β) is increased. Said differently, the less constrained pattern exhibits a broader range of polygon sizes than the more constrained pattern. Moreover, for a given sample "test box" drawn within the pattern, a change in the area of the test box affects the range of % polygon are for a given pattern. As the area of the test box decreases, the variability in % polygon area increases. Conversely, as the area of the test box increases, beyond a certain point the % polygon area remains constant throughout the pattern. The more constrained material of (larger β) displays a much narrower range of % polygon area and converges to a constant % polygon area at a smaller test box size than a less constrained material. Further, for consistency in physical properties throughout the web more constrained tessellations exhibit less variation in aerial density, i.e., the localized number of protrusions and corresponding protrusions wells, per unit area.

Based upon these observations, it would be apparent that a predictable level of consistency may be designed into the patterns generated according to the preferred method of the present invention even though amorphousness within the pattern is preserved. Accordingly, three-dimensional, amorphous-patterned, nesting-resistant materials may be formed with statistically-predictable geometric and physical material properties.

Referring once again to the drawings, and more particularly to FIG. 2, there is shown a plan view of a representative three-dimensional, nesting-resistant sheet material suitable for use as a storage wrap material of the present invention, which is generally indicated as 10. FIG. 2 represents an amorphous two-dimensional pattern generated by the above-described method utilizing a constraint factor of 0.75. Material 10 has a plurality of non-uniformly shaped and sized, preferably hollow, protrusions 12, surrounded by spaces or valleys 14 therebetween, which are preferably interconnected to form a continuous network of spaces within the amorphous pattern. FIG. 2 also shows a dimension A, which represents the width of spaces 14, measured as the substantially perpendicular distance between adjacent, substantially parallel walls at the base of the protrusions. In a preferred embodiment, the width of spaces 14 is preferably substantially constant throughout the pattern of protrusions.

Protrusions 12 of the present invention are generated with non-uniform size and shape so that material 10 may be wound onto a roll without nesting occurring between layers of material within the roll. The nesting-resistant feature is achieved because the amorphous pattern of the protrusions, as discussed above, limits the ability of the face of one layer to align with the back of another layer whereby the protrusions of one layer enter the depressions formed behind each protrusion in an adjacent layer. The benefit of narrow constant-width spaces between protrusions is that protrusions 12 cannot also enter spaces 14 when layers of material 10 are placed face to face.

Protrusions 14 are preferably spaced center to center an average distance of approximately two protrusion base diameters or closer, in order to minimize the volume of valleys between protrusions and hence the amount of substance located between them. For applications where it is intended that the protrusions be deformable, the protrusions 14 preferably have heights which are less than their diameters, so that when they deform, they deform by substantially inverting and/or crushing along an axis which is substantially perpendicular to a plane of the material. This protrusion shape and mode of deforming discourages protrusions 14 from folding over in a direction parallel to a plane of the material so that the protrusions cannot block a substance present in the valley between them from contact with a target surface.

FIG. 3 depicts a fragmentary elevational cross-section of material 10 taken at a location where a complete protrusion 12 and both adjoining spaces or valleys 14 can be seen in cross-section. In this view, the upper surface of the web which faces the viewer of FIG. 2, and which includes the projecting portions of the protrusions 12, is identified with the numeral 15, and is referred to hereafter as the male side of the material. Correspondingly, the lower surface of the web facing away from the viewer of FIG. 2, which includes the openings of the hollow portions of the protrusion 12, is identified with the numeral 17, and is referred to hereafter as the female side of the material.

FIG. 3 shows a substance 16 added to spaces 14, as well as to the hollow underside of the protrusion 12, in accordance with the teachings of commonly-assigned, co-pending, concurrently-filed U.S. patent application Ser. No. 08/744,850, Attorney's Docket No. Case 5922R, filed Nov. 8, 1996, in the names of Peter W. Hamilton and Kenneth S. McGuire, now U.S. Pat. No. 5,871,607, entitled "Material Having A Substance Protected by Deformable Standoffs and Method of Making", the disclosure of which is hereby incorporated herein by reference. Substance 16 partially fills the spaces 14 so that an outer surface of protrusions 12 remain external to the surface level of substances 16 such that the protrusions prevent the substances 16 on the male side of the material from making contact with external surfaces. With regard to the male side of the material, substances 16 partially fills the hollow protrusions such that the reverse side of the valleys or spaces between respective protrusions serves an analogous function in preventing substances 16 within the protrusions from making contact with external surfaces. Substances within different sides of the material 10 and/or within different geometrically-distinct zones within a side of material 10 need not be the same substance and could in fact be distinctly different substances serving distinctly different functions.

"Substance" is defined in this invention as any material capable of being held in open valleys and/or depressions of a three dimensional structure. In the present invention, the term "substance" can mean a flowable substance which is substantially non-flowing prior to delivery to a target surface. "Substance" can also mean a material which doesn't flow at all, such as a fibrous or other interlocking material. "Substance" may mean a fluid or a solid. Adhesives, electrostatics, mechanical interlocking, capillary attraction, surface adsorption, and friction, for example, may be used to hold the substances in the valleys and/or depressions. The substances may be permanently held in the valleys and/or depressions, or the substances may be intended to be released therefrom when exposed to contact with external surfaces or when the three dimensional structure is deformed, heated, or otherwise activated. Of current interest in the present invention include substances such as gels, pastes, foams, powders, agglomerated particles, prills, microencapsulated liquids, waxes, suspensions, liquids, and combinations thereof.

The spaces in the three-dimensional structure of the present invention are normally open; therefore it is desirable to have substances stay in place and not run out of the structure without an activation step. The activation step of the present invention is preferably deformation of the three-dimensional structure by compression. However, an activation step to cause substance to flow could be heating the material to above room temperature or cooling it below room temperature. Or it could include providing forces excessive of the earth's gravity. It could also include other deforming forces, such as tensile forces and combinations of these activation phenomena.

The term "deformable material" is intended to include foils, polymer sheets, cloth, wovens or nonwovens, paper, cellulose fiber sheets, co-extrusions, laminates, and combinations thereof. The properties of a selected deformable material can include, though are not restricted to, combinations or degrees of being: porous, non-porous, microporous, gas or liquid permeable, non-permeable, hydrophilic, hydrophobic, hydroscopic, oleophilic, oleophobic, high critical surface tension, low critical surface tension, surface pre-textured, elastically yieldable, plastically yieldable, electrically conductive, and electrically non-conductive. Exemplary materials include wood, metal, rigid polymer stock, ceramic, glass, cured resin, thermoset materials, cross-linked materials, rubber, frozen liquids, concrete, cement, stone, man-made materials, etc. Such materials can be homogeneous or composition combinations.

In a particularly preferred embodiment, protrusions 14 have an average base diameter of about 0.015 inches (0.038 cm) to about 0.030 inches (0.076 cm), and more preferably about 0.025 inches (0.064 cm). They also have an average center-to-center spacing of from 0.03 inches (0.08 cm) to 0.06 inches (0.15 cm), and more preferably about 0.05 inches (0.13 cm) spacing. This results in a high number density of protrusions. The more protrusions per unit area, the thinner the piece of material and protrusion walls can be in order to resist a given deformation force. In a preferred embodiment the number of protrusions per square inch exceeds 200 and the protrusions occupy from about 30% to about 70% of the protrusion side of the piece of material. They have a protrusion height of about 0.004 inches (0.010 cm) to 0.012 inches (0.030 cm), and more preferably about 0.006 inches (0.015 cm) height. The preferred material is 0.0003 inch (0.0076 mm) nominal thickness high density polyethylene (HDPE).

For fabrication of an adhesive-containing, three-dimensional, nesting-resistant sheet material, a preferred layer of substances 16 is preferably a latex pressure sensitive adhesive about 0.001 inch (0.025 mm) thick. Even more preferably, layer of substances 16 may be about 0.0005 inch (0.013 mm) thick layer to about 0.002 inch (0.051 mm) thick layer of hot melt adhesive, specification no. Fuller HL-2115X made by H. B. Fuller Co. of Vadnais Heights, Minn. Any adhesive can be used which suits the needs of the material application. Adhesives may be refastenable, releasable, permanent, or otherwise. The size and spacing of protrusions is preferably selected to provide a continuous adhesive path surrounding protrusions so that air-tight seals may be made with a target surface.

Film materials may be made from homogeneous resins or blends thereof. Single or multiple layers within the film structure are contemplated, whether co-extruded, extrusion-coated, laminated or combined by other known means. The key attribute of the film material is that it be formable to produce protrusions and valleys. Useful resins include polyethylene, polypropylene, PET, PVC, PVDC, latex structures, nylon, etc. Polyolefins are generally preferred due to their lower cost and ease of forming. Preferred material gauges are about 0.0001 inches (0.0025 mm) to about 0.010 inches (0.25 mm). More preferred gauges are from about 0.0002 inches (0.005 mm) to about 0.002 inches (0.051 mm). Even more preferred gauges are from about 0.0003 inches (0.0076 mm) to about 0.001 inches (0.025 mm).

Providing a film modulus of elasticity sufficiently high to minimize film stretch during use is beneficial to sealing material 10 to a target surface. Stretched film results in residual forces parallel to the plane of adhesive contact, which may cause a weak adhesive bond to break. The larger and more closely spaced the protrusions, the greater the likelihood of stretch occurring in a given film. Although elasticity in material 10 is believed to be undesirable for use as a container wrap which seals to a container, there are potentially many other uses for an elastic material containing a pattern of substance. Reducing the protrusion spacing to the closest possible spacing which is manufacturable may increase material stretch, but it may be beneficial in reducing the volume of substance between protrusions. Different applications for the formed material of the present invention will dictate ideal size and density of protrusions, as well as the selection of the substances used therewith.

The material property "beam strength" of the three-dimensional sheet material was mentioned above in terms of the beam strength preventing significant nesting of any region of material surrounding a given protrusion even in the event that that protrusion finds itself superimposed over a single matching or larger depression of compatible shape since the protrusions surrounding the single protrusion of interest will differ in size, shape, and spacing from those surrounding the other protrusion/depression. Beam strength is thus an important factor to consider when selecting the material type and thickness, as well as the density and pattern of protrusions. It has been observed that in general larger numbers of smaller protrusions provide a greater level of beam strength for a given material type and thickness than a smaller number of larger protrusions. Said differently, thinner and more conformable materials may be utilized and still realize the non-nesting advantages of the present invention through the use of an amorphous pattern having generally comparatively small, comparatively high number density protrusions.

It is believed that the protrusion size, shape and spacing, the web material properties such as flexural modulus, material stiffness, material thickness, hardness, deflection temperature as well as the forming process determine the strength of the protrusion. The forming process is important in polymer films for example, since "cold forming" or embossing generates residual stresses and different wall thickness distributions than that produced by thermoforming at elevated temperatures. For some applications it is desirable to provide a stiffness (deformation resistance) which is sufficient to withstand a pressure of at least 0.1 pounds per square inch (0.69 kPa) without substantially deforming protrusions to where the substance contacts an external surface. An example of this requirement would be the need to wind the web onto a roll for transport and/or dispensing. Even with very low in-wound pressures of 0.1 pounds per square inch (0.69 kPa), a residual in-wound pressure in the interior of the roll may deform protrusions in the web sufficiently to bring the overlaying web layers into contact with the substance. A "threshold" protrusion stiffness is required to prevent this winding damage from occurring. Similarly, when the web is stored or dispensed as discrete sheets, this "threshold" stiffness is required to prevent premature activation of the product due to the weight of overlaying layers of sheets or other forces, such as forces induced by shipping vibrations, mishandling, dropping and the like.

Deformation mode and force can be influenced by the sidewall thickness profile to provide more desired results. A protrusion's sidewall connects the outermost portion of the protrusion to the unformed material adjacent to base perimeter of the protrusion. The sidewall as defined may also contain a peripheral region substantially within the outermost portion which is substantially thinner than the interior region of the outermost portion. Protrusions where at least a portion of the sidewalls are substantially thinner than the unformed material adjacent to the base perimeter are believed preferred for deformation by the user. Sidewalls that are also substantially thinner in at least a portion of the sidewall as compared to the material at the outermost portion of the protrusion also beneficially bias the deformation to occur primarily within the sidewall structure.

In structures containing relatively small protrusions, as found in high number density protrusion patterns, such thinner sidewall gauges can be particularly useful.

Protrusion 12 have sidewalls 22, which become thinned when protrusions 12 are formed, to help ensure that protrusions 12 deform as intended. High density polyethylene is preferred over low density polyethylene because the former can be made thinner for the same protrusion deform strength and because once deformed, HDPE protrusions do not tend to rebound toward their undeformed initial configuration as do the LDPE protrusions.

Protrusion 12 preferably have a convex polygonal base shape, the formation of which is described hereinafter. By convex polygonal shape, it is meant that the bases of the protrusions have multiple (three or more) linear sides, which form no externally measured angle of less than 180° with any adjacent side. Of course, alternative base shapes are equally useful. However, the preferred base shape is believed to be most easily generated. Polygons preferably interlock in the plane of the lower or female surface 17, as in a tessellation, to provide constant width spacing between them. The width A of spaces 14 may be selected depending upon the volume of substance desired between protrusions. Preferably width A is always less than the minimum protrusion dimension of any of plurality of protrusions 12. The area occupied by plurality of protrusions 12 is preferably from about 30% to about 70%, more preferably about 50%, of the available area of sheet of material 10, as measured parallel to plane 20.

Figure 4:
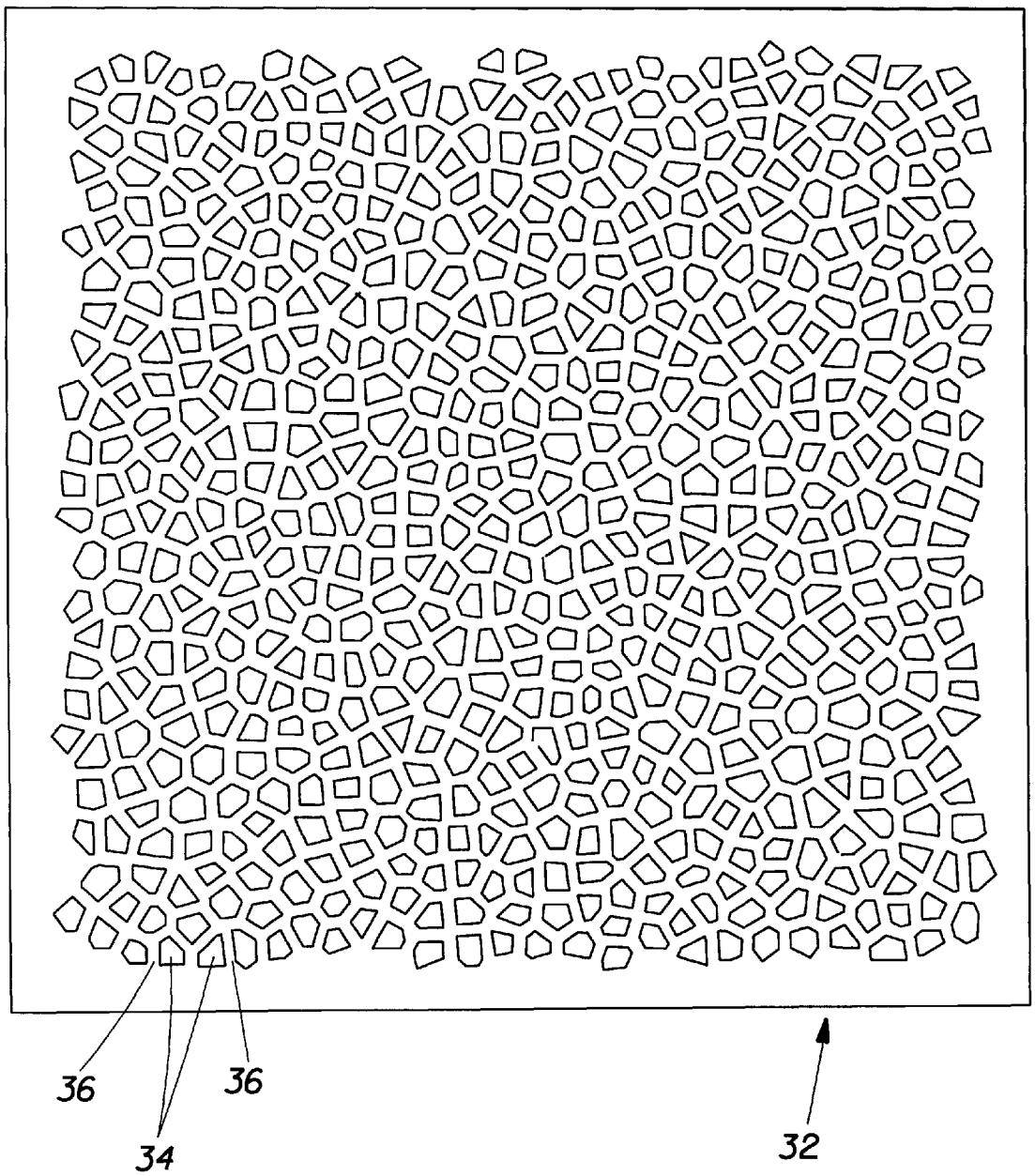
FIG. 4 is a plan view of a three-dimensional forming structure suitable for forming a three-dimensional, nesting resistant sheet material such as that of FIG. 3.
Figure 5:
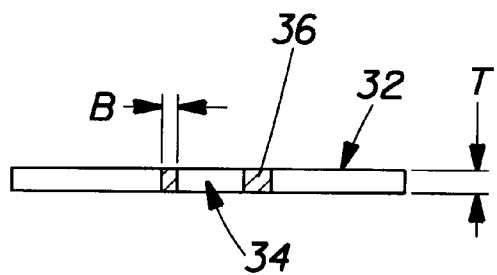
FIG. 5 is a partial elevational sectional view of the three-dimensional forming structure of FIG. 4.
Figure 6:
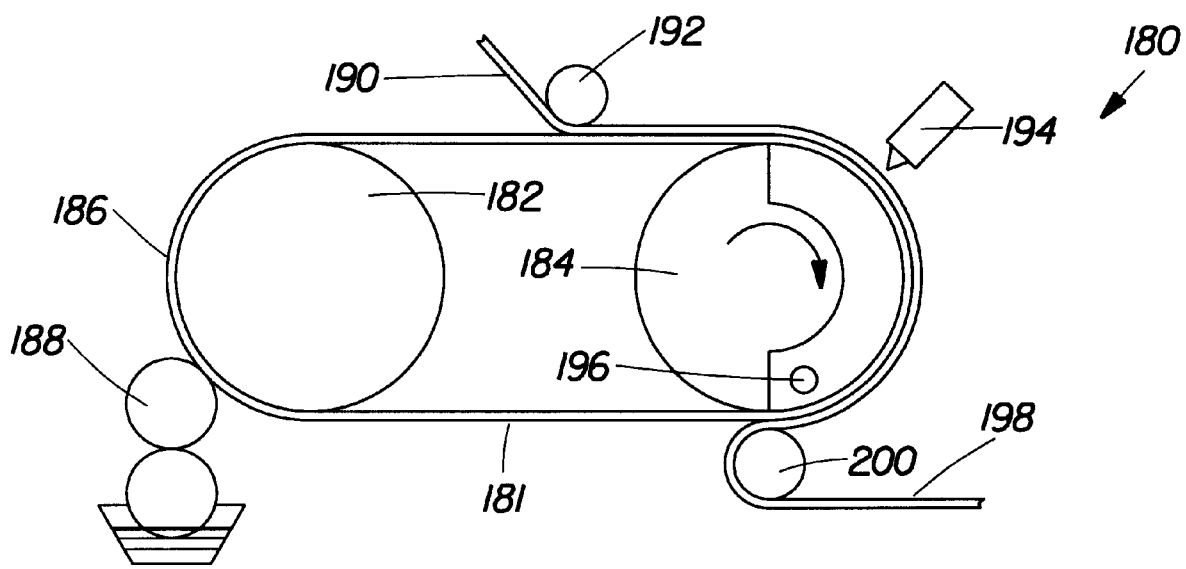
FIG. 6 is a schematic illustration of a representative apparatus suitable for forming a storage wrap material in accordance with the present invention.

FIGS. 4–6 disclose a suitable method and apparatus for making material 10, the method generally indicated as 30. Method 30 is representative and may be modified or tailored to suit a particular size, composition, etc. of the resulting material 10. Method 30 utilizes a forming surface 32, which is preferably a three-dimensional screen having recesses 34 and lands 36 between recesses 34. Such a forming structure or forming structure would constitute a female-type forming structure which, in use, would form corresponding male protrusions in the structure-contacting side of the formed material. Alternatively, forming surface 32 could comprise a three-dimensional forming structure of the male variety by having raised pins 34 of the desired polygonal shape having recesses 36 between and around the pins 34. In use, such a forming structure would form corresponding female depressions in the structure-contacting side of the formed material.

More particularly, FIG. 4 depicts a forming surface which could be utilized to form a corresponding three-dimensional material 10 such as depicted in FIG. 2. When a material 10 is thermoformed over forming surface 32, protrusions 12 are preferably formed by drawing them into recesses 34 with vacuum when material 10 is heated to a softening temperature, and then maintaining protrusions 12 drawn into recesses 34 while material 10 cools to a solidification temperature. In this method, lands 36 define the bases of spaces 14 between protrusions 12. Protrusion 12 are preferably formed with sidewalls 22 being as nearly perpendicular to plane 20 as possible, but with some taper being typical. Outermost ends of protrusions 12 may domed or more truncated in shape so as to form frustums of the corresponding polygonal shape.

Material 10 may be vacuum thermoformed, embossed, or hydroformed, or formed by other forming means commonly known in the art for permanently deforming thin materials.

FIG. 4 shows a preferred forming screen 32 comprising interconnected lands 36 surrounding polygonal recesses 34. Lands 36 are preferably made of stainless steel and coated with a release agent. Most preferably, screen 32 is made into a continuous belt 38, as shown in FIG. 6. Alternatively, screen 32 could be utilized in flat plate-like form or formed into a rigid drum. FIG. 5 depicts a partial cross-sectional view of forming screen 32 taken at a location which depicts a cross-section through two consecutive lands. Lands 36 have a dimension B which represents the land width, which is preferably constant as measured between substantially parallel adjacent land edges, and a dimension T which represents screen thickness.

The amorphous pattern of the forming screen is preferably generated in accordance with the method described above.

Methods of production can influence the sidewall thickness profile such as in the use of a forming screen with essentially straight screen walls which define the forming screen hole. Such a process allows for substantially thinner sidewall thickness since the protrusion is freely drawn from the base perimeter into the forming screen recess to the point of contact with the internal backup screen. The internal backup screen's purpose is to prevent further drawing of the protrusion. This approach yields a more varied gauge profile within the sidewalls.

It has been discovered while reducing to practice the present invention that when using hot melt adhesive for the substance, thermoforming behaves differently than when other substances are processed. The difference is that protrusions, which are formed when hot melt adhesive has been applied to the forming surface, tend to exhibit more thinning in their sidewalls. It is believed that the hot melt adhesive cools and solidifies when contacting the metal forming surface and thereby prevents web material in contact with the adhesive from being drawn into the recesses, so that uniform thickness valleys result. With other substances, such as latex adhesive, less thinning of protrusion sidewalls occurs, presumably because some of the web material in contact with the adhesive on the lands or pin tops of the forming surface flows into the recesses during thermoforming.

FIG. 6 shows a suitable and presently preferred method and apparatus for making a material such as material 10 of the present invention, which is generally indicated as 180. The formed material is preferably transparent or translucent, so that it may be accurately positioned before being deformed. Transparency, however, introduces a new problem of determining on which side of the three-dimensional structure the substance is located, in order to know which side to place against a target surface. Substance side identification can be solved by placing indicia on the surface of the three dimensional structure, by coloring the substance a different tint than the three dimensional structure, or by providing a laminated material structure of different tints, for example. In the case of labels, transparency may not be needed since material edges may be used for proper positioning.

Micro-texturing the material during forming may also be useful, such as in producing a distinction between one side of the material and the other side. Micro-texturing of the outermost surface features of the three dimensional structure may be achieved in the present invention, for example, by drawing the piece of material into forming screen recesses and against a micro-textured surface, such as a vacuum drum having tiny apertures therein.

Forming screen 181 is threaded over idler pulley 182 and a driven vacuum roll 184. Forming screen 181 is preferably a 0.005 inch (0.013 cm) thick, 12.5 inch (31.8 cm) wide, 6 foot (183 cm) circumference stainless steel belt, having the desired protrusion pattern etched as recesses in the belt. Covering the outer surface of vacuum roll 184 is a 195 mesh seamless nickel screen having a diameter of 8.63 inches (21.9 cm), which serves as a porous backing surface for forming screen 181.

For producing a pressure sensitive adhesive containing material, a substance 186, preferably hot melt adhesive, is coated onto forming screen 181 by a substance applicator 188 while forming screen 181 travels at about 20 feet (610 cm) per minute. A material 190, for example, a HDPE film web about 0.0005 inches (0.0013 cm) thick, is brought into contact with the substance-coated forming screen at material infeed idler roll 192. Hot air at approximately 600° F. (316° C.) and flowing at approximately 11.25 SCFM (0.32 cubic meters/minute) is directed radially at material 190 by a hot air source 194 as the material passes over vacuum roll 184 and as vacuum is applied to forming screen 181 through vacuum roll 184 via fixed vacuum manifold 196 from a vacuum source (not shown). A vacuum of approximately 12 inches of mercury (40.6 kPa) is applied as the material is heated by hot air source 194. A formed, substance coated material 198 is stripped from forming screen 181 at stripping roll 200.

Stainless steel forming screen 181 is a fabricated, seamed belt. It is fabricated in several steps. The recess pattern is preferably developed by a computer program according to the method described above and is preferably printed onto a transparency to provide a photomask for photoetching. The photomask is used to create etched and non-etched areas. The etched material is typically stainless steel, but it may also be brass, aluminum, copper, magnesium, and other materials including alloys. Methods of making metal screens by photoetching are described in more detail in commonly owned U.S. Pat. No. 4,342,314 to Radel and Thompson, U.S. Pat. No. 4,508,256 to Radel et al., and U.S. Pat. No. 4,509,908 to Mullane, Jr., the disclosures of which are hereby incorporated herein by reference.

Additionally, the recess pattern may be etched into photosensitive polymers instead of metals. Examples are described along with a methods of making polymer forming screens in commonly owned U.S. Pat. No. 4,514,345 to Johnson et al., U.S. Pat. No. 5,098,522 to Smurkoski et al., U.S. Pat. No. 4,528,239 to Trokhan, and 5,245,025 to Trokhan, the disclosures of which are hereby incorporated herein by reference.

Next, the forming screen is converted into a continuous belt by butt welding the ends together, using either laser or electron beam welding. This produces a nearly undetectable seam, which is needed to minimize disruptions in the recess pattern. The final step is coating the endless belt with a low critical surface tension (non-stick) coating, such as a Series 21000 proprietary release coating made by and applied by Plasma Coatings of TN, Inc., located in Memphis, Tenn. It is believed that this coating is primarily an organo-silicone epoxy. As applied to a stainless steel forming screen used in the methods of the present invention, this coating provides a critical surface tension of about 18 dynes/cm. Other materials which may prove suitable for providing reduced critical surface tension include paraffins, silicones, PTFE's, and the like. This coating allows the formed material to be removed from the belt without undue stretching or tearing.

A belt forming screen is believed advantageous to a flat plate or a drum forming screen because a belt enables screen patterns and pattern lengths to be changed more easily and larger patterns may be used without having massive rotating members. However, depending upon the desired quantity and dimensions of the material 10 to be formed it may be equally suitable to fabricate the forming structure as a flat plate or rigid drum, and/or other forming structures and methods known in the art.

Because the same common forming screen is used to transfer the substance to the material as is used to form the protrusions, the substance pattern is conveniently registered with the protrusions. In the preferred embodiment, the top surface of forming screen 32 is continuous except for recesses 34; thus, the substance pattern is totally interconnected in this configuration. However, if a discontinuous pattern of substance were coated onto forming screen 32, a discontinuous substance pattern between protrusions would result.

In accordance with the preferred method of manufacturing the three-dimensional, nesting-resistant sheet material 10, the three-dimensional protrusions are unitarily formed from the sheet of deformable material itself and are hollow structures with depressions in one side which preferably each have a size and three-dimensional shape corresponding substantially with the size and three-dimensional shape of their respective protrusion. However, it may also be desirable for some applications to utilize solid protrusions unitarily, integrally, or separately formed from (and applied to) the sheet of material and which may or may not be deformable.

In general, the present invention is a storage wrap material which may take the form of a three-dimensional sheet material which is activated by applying a compressive force so that the structure collapses to expose an adhesive to contact with external surface(s). However, the scope of the invention also applies to storage wrap materials which are activatible by means other than compression. For example, the inventors have found that a tensile force applied to the same three-dimensional structure can cause it to plastically deform longitudinally and thereby contract in caliper or thickness to similarly expose or release substance. It is believed that under sufficient tension, the material between protrusions deforms in response to forces in the plane of the material and that protrusions are thereby elongated in the same direction. When the protrusions are elongated, they are reduced in height. With enough elongation the protrusions are reduced in height to where the substances between them, in them, or both are exposed.

For a one inch wide strip of material 10, made from 0.0003 inch (0.0076 mm) thick HDPE and formed to have protrusions of 0.006 inches (0.152 mm) height and 0.030 inches (0.762 mm) diameter, spaced 0.045 inches (1.14 mm) apart, the tensile force found necessary to cause protrusions to expose a 0.001 inch (0.025 mm) thick coating of adhesive in the valleys between protrusions is approximately 0.80 pounds (0.36 kg) per inch of strip width.

A combination of compression and tensile forces may be applied to the material of the present invention in order to expose a substance from within the three-dimensional structure. Although in a preferred embodiment of the present invention, the tensile force necessary to achieve sufficient deformation of said three-dimensional structure in order to expose substance to an external surface is significantly greater than a compressive force to achieve the same result, a structure may be designed which is more easily deformed by a tensile force applied in a specific planar direction. For example, a structure may have parallel waves instead of protrusions and the waves may be easily flattened by stretching the structure perpendicular to the waves but in the plane of the waves. Tensile responsive structures and the principles behind them are disclosed in commonly-assigned U.S. Pat. No. 5,518,801 to Chappell et al., the disclosure of which is hereby incorporated herein by reference.

In another example, heat could be applied to cause the same structure made of shrinkable film to reduce in thickness to similarly release or expose the substance.

As described herein, different substances can be deposited on the opposing faces of the formed material. Multiple substances can be located on the same face of the material either geometrically spaced from each other or commingled. Substances can be partially layered. An example is a layer of adhesive adjacent to the material surface with a solid particulate adhered to the exposed side of the adhesive layer. In addition, it is contemplated that it may be desirable for certain applications to have protrusions extending outwardly from both sides of the formed material, such that both sides are active sides with deformable protrusions.

A pattern of protrusions can be superimposed either on a similar dimensional scale or on a different dimensional scale such as a single or multiple "microprotrusion" pattern located on the tops of other larger protrusions.

Additional details of the process of FIG. 6, as well as additional details regarding three-dimensional materials described above may be found in the aforementioned and incorporated commonly-assigned, co-pending, concurrently-filed U.S. patent application Ser. No. 08/744,850, Attorney's Docket No. Case 5922R now U.S. Pat. No. 5,871,607.

While under some circumstances it may be acceptable or desirable to design the storage wrap material so as to form a discontinuous bond pattern with itself or another target surface, such as by having an intermittent or discontinuous layer of adhesive on its active surface, it is presently preferred that the storage wrap material be designed so as to exhibit the ability to form a continuous seal or bond with itself and with any sufficiently continuous target surface.

Figure 7:
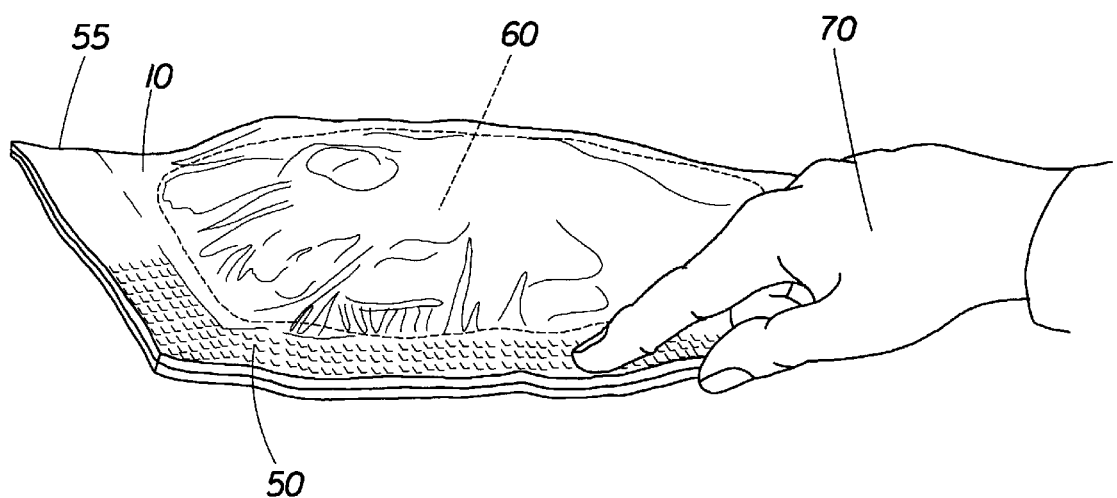
FIG. 7 is a perspective view of the storage wrap material of the present invention being formed into a unitary package around an item to be stored by bonding the material to itself around the item.
Figure 8:
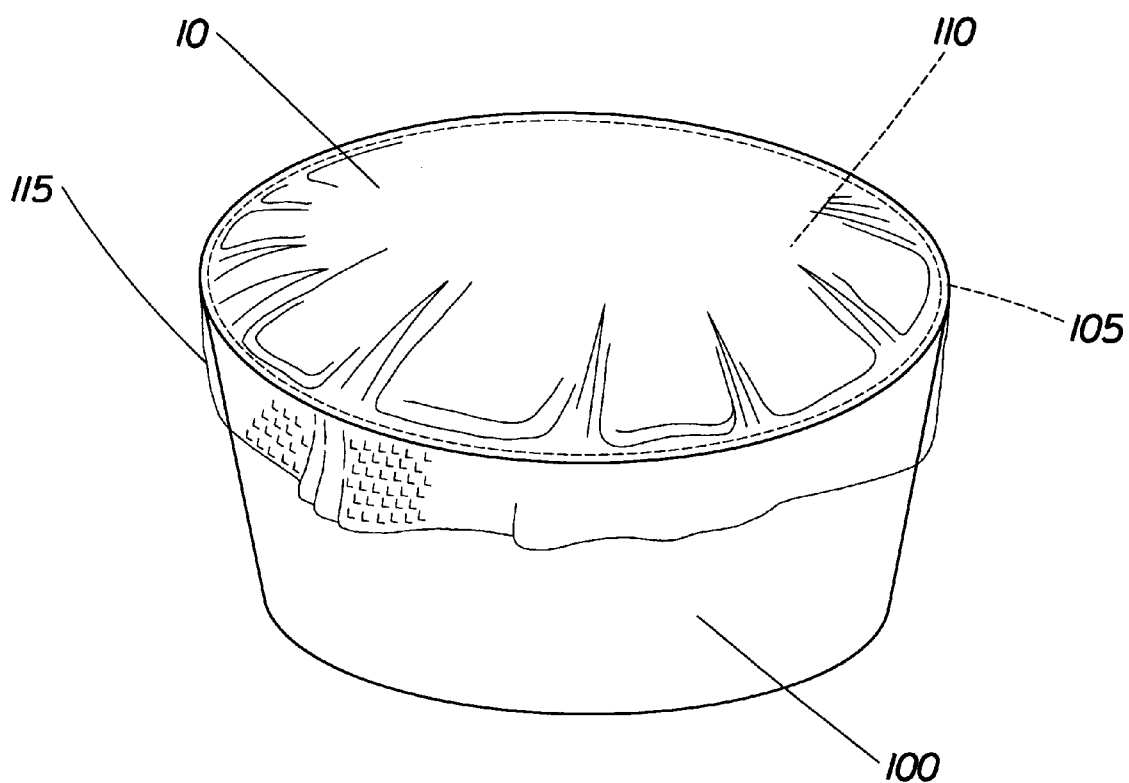
FIG. 8 is a perspective view of the storage wrap material of the present invention being utilized in combination with a semi-enclosed container to form a closed container.
Figure 9:
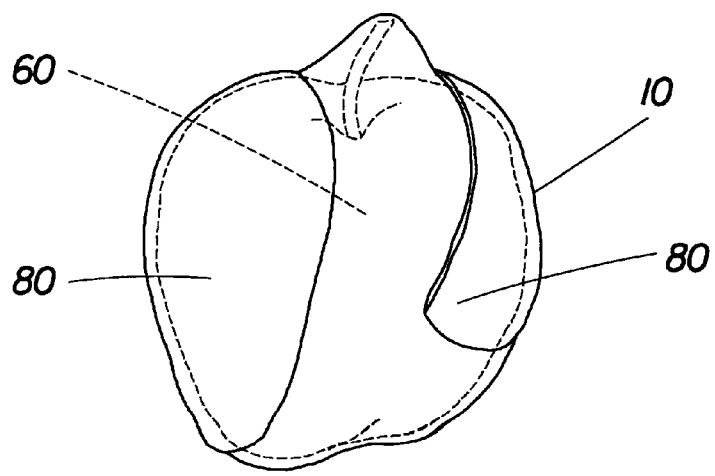
FIG. 9 is a perspective view of the storage wrap material of the present invention being formed into a unitary package around an item to be stored by bonding overlying portions of the material to itself over the item.

FIGS. 7–9 depict representative applications of interest for the storage wrap material 10.

More particularly, FIG. 7 depicts storage wrap material 10 utilized independently to form a closed container for an item 60. For use in this fashion, a one-sided version of storage wrap material 10 is preferably utilized such that only one side of the material is active, although a two-sided material could also be utilized. To utilize storage wrap material 10 in this fashion, the material is wrapped or folded around the desired item 60 so as to leave a marginal edge extending outwardly beyond the maximum dimensions of the item 60. As depicted in FIG. 7, the web of storage wrap material 10 has been folded over and around the item 60 by folding the material along a folded edge 55 and forming a fin-type seal 50 around the remaining perimeter, in this instance three sides, of the item 60. In this deployment, the storage wrap material 10 is bonded or adhered to itself in a face-to-face orientation wherein both active sides of the material are in contact with one another. Accordingly, when a user 70 activates the adhesive on at least one, and preferably both, of the overlying or overlapping portions of the material in the region of the fin seal 50 the overlying portions are firmly adhered together to complete the enclosure of the item 60. Alternatively, rather than folding a larger web of material upon itself to form an enclosure, two or more discrete smaller pieces of storage wrap material 10 may be utilized by wrapping them over the item 60 and sealing them to one another in face-to-face or face-to-back orientation.

FIG. 8 depicts another useful deployment of storage wrap material 10 as the closure of a semi-enclosed, rigid or semi-rigid container 100. In the configuration of FIG. 8, a combination container structure is thus illustrated wherein the storage wrap material is adhered to the rim portion 105 of the container which circumscribes the opening 110 to form a corresponding closure for the opening. Although the storage wrap material 10 would form an adequate barrier seal if only applied to the surface of the rim 105 which is in the plane of the opening 110, as depicted in FIG. 8 the storage wrap material 10 may also be applied so as to effect a seal over an additional area around the periphery of the rim 105 by bonding to the wall portion 115 of the container which extends in a direction substantially normal to the plane of the opening. Effective sealing may also be accomplished by bonding the storage wrap material only to the wall portion 115 of the container. Where such a closure completely encloses the contents (not shown) of the container 100, the contents are protected from the exterior environment outside the container and are also contained and protected from loss.

Containers such as container 100, which as shown has no protruding structures for cooperating with storage wrap 10, are frequently constructed of such rigid or semi-rigid materials such as metals, glass, ceramics, plastics, or wood which have a comparatively smooth and uniform surface. Accordingly, storage wrap material 10 in accordance with the present invention activates to provide the desired level of adhesive force in combination with such non-conforming, rigid or semi-rigid surfaces so as to effectively form a closure for such containers. In addition, the storage wrap material may also be utilized in conjunction with openings in the plane of a wall of a container as well as openings which are formed at an end, etc. of a container substantially normal to adjacent wall surfaces. Such versatility is due to the adhesive properties of the storage wrap material which, unlike dead-fold wrap materials such as waxed paper or aluminum foil, enable the storage wrap materials of the present invention to form a suitable seal without the need to form a wrap angle around a rim, lip, or other structure adjacent the container opening.

FIG. 9 depicts yet another common application for storage wrap 10, wherein a discrete web of storage wrap 10 of the desired dimensions is wrapped continuously around an item 60 so as to enclose the item 60 completely. Edge portions 80 of the storage wrap 10 which overly the item and overly other portions of the storage wrap 10 are adhered to such other portions after activation such that they are secured in sealing relationship. This mode of item enclosure is particularly useful when the item has an irregular shape, such as the item 60 depicted in FIG. 9. In this mode of deployment, the storage wrap 10 is preferably oriented with the active side facing inwardly toward the item 60 such that the storage wrap may be activated over the item to provide additional security against shifting or loosening of the material. Alternatively, the storage wrap 10 could be wrapped around the item with the active side facing outwardly if adherence to the item is not desired. In either mode of deployment, the overlying portions 80 of the storage wrap material 10 will be activated and adhered to one another in face-to-back relation with one of the overlying portions being activated to provide the adhesive property and the other overlying portion being non-activated and hence a passive target surface.

If a two-sided activatible storage wrap material were utilized in the above example, then either or both of the superimposed face and back portions in the overlying portions 80 could be activated to effect a sealed region.

The improved storage wrap materials of the present invention may be employed to enclose a wide variety of items, both perishable and non-perishable. Such items may include single items within a given container/package system, as well as multiple items of the same or different types. Items enclosed may in fact be containers or packages which are themselves to be enclosed, such as a group of cartons wrapped together upon a pallet, for example. The items may be loosely grouped together within a single chamber within the container, or may be segregated within different chambers or compartments formed by the storage wrap material itself or other features of the container.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An improved storage wrap material comprising:
    (a) a sheet of non-porous material having a first side and a second side, said first side comprising an active side exhibiting an adhesion peel force after activation by a user which is greater than an adhesion peel force exhibited prior to activation by a user and which is sufficient to form a continuous seal against any target surface, wherein a compressive force of at least about 0.1 psi is required to activate said active side, and wherein said sheet of material is linerless, such that activation of said active side requires no removal of components of said sheet of material, said sheet of material being sufficiently flexible to conform readily to any desired surface and having sufficiently small resiliency that it does not exert undue restorative forces which would tend to cause said sheet of material to break contact with such a desired surface.

2. The improved storage wrap material of claim 1, wherein said active side is activatible by an externally applied force exerted upon said sheet of material.

3. The improved storage wrap material of claim 2, wherein said active side is activatible by an externally applied compressive force exerted in a direction substantially normal to said sheet of material.

4. The improved storage wrap material of claim 2, wherein said active side is activatible by an externally applied tensile force exerted in a direction substantially parallel to said sheet of material.

5. The improved storage wrap material of claim 1, wherein said active side exhibits an adhesion peel force of at least about 1 ounce per inch width after activation by a user.

6. The improved storage wrap material of claim 1, wherein said active side exhibits an adhesion peel force of between about 1 and about 2.5 ounces per inch width after activation by a user.

7. The improved storage wrap material of claim 1, wherein said active side may be selectively activated in discrete regions by a user.

8. The improved storage wrap material of claim 1, wherein said active side may be activated by compression against a target surface.

9. The improved storage wrap material of claim 1, wherein said adhesion peel force after activation is sufficient to form a barrier seal against a target surface, said seal exhibiting barrier properties at least as great as those of said material and said target surface.

10. The improved storage wrap material of claim 1, wherein both said first side and said second side comprise active sides of said material.

11. The improved storage wrap material of claim 1, wherein said active side when activated forms a permanent bond with a target surface.

12. The improved storage wrap material of claim 1, wherein said active side when activated forms a releasable bond with a target surface.

13. The improved storage wrap material of claim 1, wherein said active side includes a pressure sensitive adhesive.

14. The improved storage wrap material of claim 1, wherein said sheet of material comprises a polymeric film material.

15. The improved storage wrap material of claim 14, wherein said polymeric film material is substantially translucent.

16. The improved storage wrap material of claim 1, wherein said active side comprises a plurality of three-dimensional non-adherent protrusions extending outwardly from said sheet of material and a pressure-sensitive adhesive surrounding said non-adherent protrusions, said adhesive having a thickness less than the height of said non-adherent protrusions before activation.

17. The improved storage wrap material of claim 16, wherein said second side includes a plurality of spaced, three-dimensional hollow depressions corresponding to said protrusions, such that said protrusions are hollow, and wherein said depressions are partially filled with a pressure-sensitive adhesive.

18. The improved storage wrap material of claim 16, wherein said protrusions are unitarily formed from said sheet of material.

19. The improved storage wrap material of claim 1, wherein said sheet of material is clingless and exhibits no adhesion peel force prior to activation by a user.

20. The improved storage wrap material of claim 1, further comprising a dispenser, said sheet of material forming a continuous web wound to form a roll of storage wrap material, said roll of storage wrap material being disposed within said dispenser.

21. The improved storage wrap material of claim 20, further comprising a core disposed within said dispenser, said sheet of material being wound upon said core to form said roll of storage wrap material.

22. The improved storage wrap material of claim 1, wherein said dispenser comprises a carton.

23. The improved storage wrap material of claim 1, wherein said dispenser includes a severing apparatus.

24. An improved storage wrap material comprising:

(a) a sheet of non-porous substantially translucent polymeric film material having a first side and a second side, said first side comprising an active side which is activatible by an externally applied compressive force exerted in a direction substantially normal to said sheet of material, said active side exhibiting an adhesion peel force after activation by a user which is greater than an adhesion peel force exhibited prior to activation by a user and which is sufficient to form a continuous seal against any target surface, wherein said active side comprises a plurality of three-dimensional non-adherent protrusions unitarily formed from and extending outwardly from said sheet of material and a pressure-sensitive adhesive surrounding said non-adherent protrusions, said adhesive having a thickness less than the height of said non-adherent protrusions before activation, wherein a compressive force of at least about 0.1 psi is required to activate said active side, and wherein said sheet of material is linerless, such that activation of said active side requires no removal of components of said sheet of material, said sheet of material being sufficiently flexible to conform readily to any desired surface and having sufficiently small resiliency that it does not exert undue restorative forces which would tend to cause said sheet of material to break contact with such a desired surface.

\* \* \* \* \*